United States Patent
Nguyen et al.

(10) Patent No.: US 9,216,220 B2
(45) Date of Patent: Dec. 22, 2015

(54) COMPOSITIONS AND METHODS FOR THERMO-SENSITIVE NANOPARTICLES AND MAGNETIC NANOPARTICLES

(75) Inventors: Kytai T. Nguyen, Grand Prairie, TX (US); Maham Rahimi, Lubbock, TX (US); Soujanya Kona, Andhra Pradesh (IN); Arthur H. Lin, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 596 days.

(21) Appl. No.: 12/937,218

(22) PCT Filed: Mar. 25, 2009

(86) PCT No.: PCT/US2009/038241
§ 371 (c)(1),
(2), (4) Date: Dec. 28, 2010

(87) PCT Pub. No.: WO2009/126441
PCT Pub. Date: Oct. 15, 2009

(65) Prior Publication Data
US 2011/0097416 A1   Apr. 28, 2011

Related U.S. Application Data

(60) Provisional application No. 61/044,039, filed on Apr. 10, 2008, provisional application No. 61/054,619, filed on May 20, 2008.

(51) Int. Cl.
| | |
|---|---|
| *A61K 9/00* | (2006.01) |
| *A61K 9/50* | (2006.01) |
| *A61K 9/51* | (2006.01) |
| *A61K 41/00* | (2006.01) |
| *A61K 49/18* | (2006.01) |
| *A61K 47/48* | (2006.01) |

(52) U.S. Cl.
CPC .......... *A61K 41/0028* (2013.01); *A61K 9/0009* (2013.01); *A61K 9/5094* (2013.01); *A61K 9/5138* (2013.01); *A61K 9/5146* (2013.01); *A61K 41/00* (2013.01); *A61K 47/4893* (2013.01); *A61K 49/18* (2013.01)

(58) Field of Classification Search
CPC .............. A61K 9/0009; A61K 9/5094; A61K 41/0028; A61K 9/5146; A61K 9/5138; A61K 41/00; A61K 49/18; A61K 47/4893
See application file for complete search history.

(56) References Cited

U.S. PATENT DOCUMENTS

| | | | | |
|---|---|---|---|---|
| 5,844,098 A | * | 12/1998 | Chao et al. | 530/395 |
| 5,929,214 A | | 7/1999 | Peters et al. | |
| 2003/0185757 A1 | | 10/2003 | Kresse et al. | |
| 2005/0069955 A1 | | 3/2005 | Plaksin et al. | |
| 2005/0175702 A1 | * | 8/2005 | Muller-Schulte | 424/486 |
| 2007/0048383 A1 | | 3/2007 | Helmus et al. | |
| 2010/0196284 A1 | * | 8/2010 | Lindner et al. | 424/9.52 |

FOREIGN PATENT DOCUMENTS

EP    1312671 A1 *  5/2003

OTHER PUBLICATIONS

Shen, Z., et al., "Preparation and characterization of thermo-responsive albumin nanospheres", Jun. 14, 2007, Int. J. Phamaceut., 346, pp. 133-142.*
Sun, Y., et al., "Magnetic separation of polymer hybrid iron oxide nanoparticles triggered by temperature", 2006, Chemical Communications, pp. 2765-2767.*
Weller, G.E.R., et al., "Targeted Ultrasound Contrast Agents: In Vitro Assessment of Endothelial Dysfunction and Multi-Targeting to ICAM-1 and Sialyl Lewisx", 2005, Biotechnology and Bioengineering, 92, pp. 780-788.*
Huang, G., et al., "Synthesis and Study of Crystalline Hydrogels, Guided by a Phase Diagram", 2004, U.Texas Thesis, pp. 1-138.*
Klein, J., et al., "Water-soluble poly(acrylamide-allylamine) derivatives of saccharides for protein-saccharide binding studies", 1995, Glycoconjugate Journal, 12, pp. 51-54.*
Gao, et al., "Thermosensitive poly(allylamine)-g-poly(N-isopropylacrylamide): synthesis, phase separation and particle formation," Polymer (2005), 46:4088-4097.
Guo, et al., "Fabrication and characterization of iron oxide nanoparticles reinforced vinyl-ester resin nanocomposites," Composites Science and Technology (2008), 68:1513-1520.
Guo, Zhanhu, et al., "Fabrication and Characterization of Iron Oxide Nanoparticles Reinforced Vinyl-Ester Resin nanocomposites," Composites Science and Technology, (2008), vol. 68, pp. 1513-1520.
International Search Report and Written Opinion for PCT/US09/38241, dated Jul. 22, 2009, 5 pages.
Mohwald, et al. "Thermosensitive poly (allylamine)-g-poly (N-isopropylacrylamide): synthesis, phase separation and particle formation," 2004.

* cited by examiner

*Primary Examiner* — Michael G Hartley
*Assistant Examiner* — Lance Rider
(74) *Attorney, Agent, or Firm* — Nevrivy Patent Law Group P.L.L.C.

(57) ABSTRACT

Provided herein are systems, methods, and compositions for polymer nanoparticles and polymer magnetic nanoparticles. More particularly, the polymer nanoparticles and polymer magnetic nanoparticles are temperature sensitive and responsive to a first temperature.

10 Claims, 32 Drawing Sheets

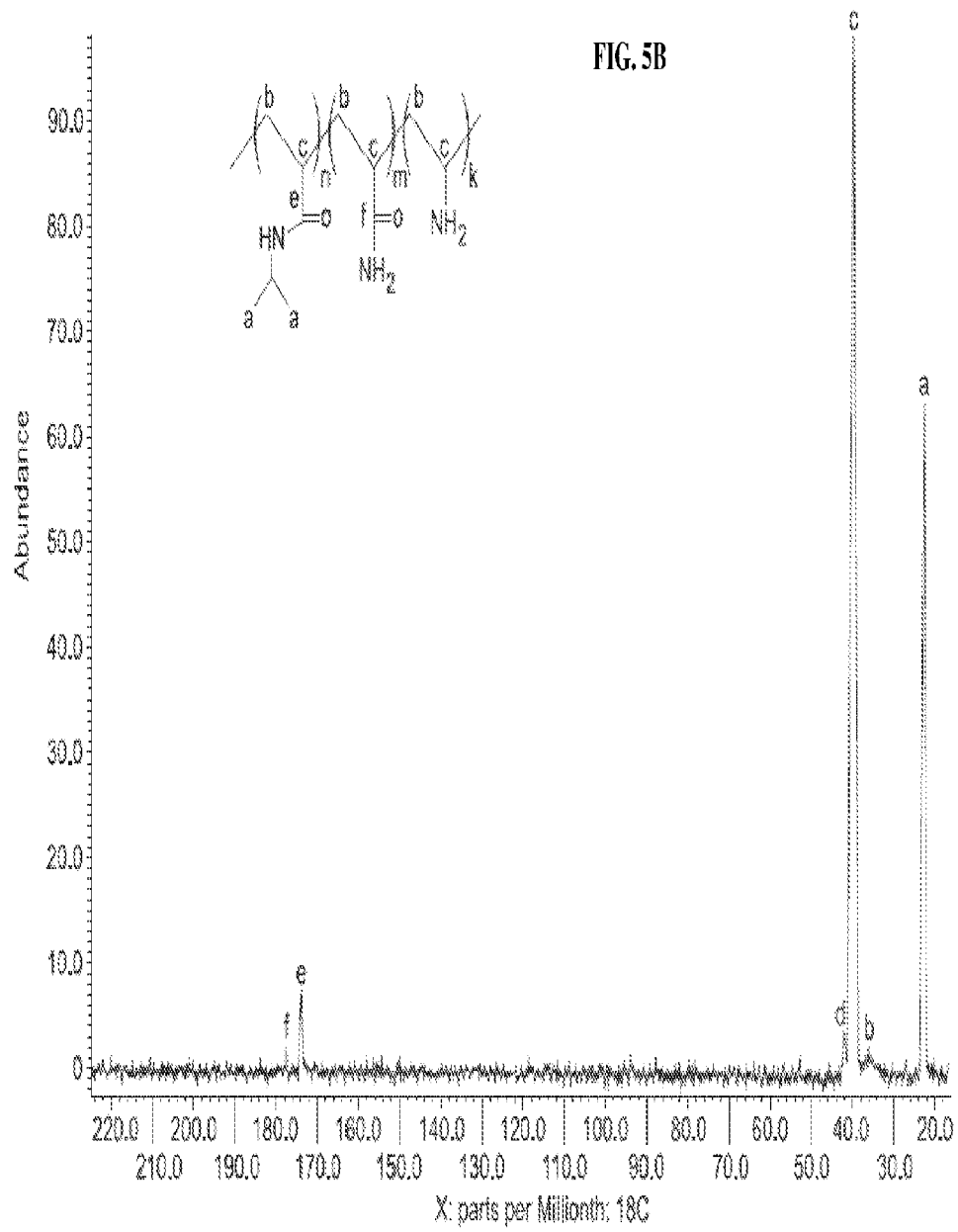

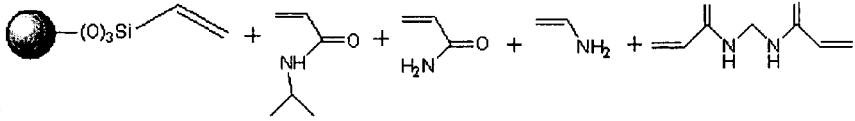
FIG. 12C
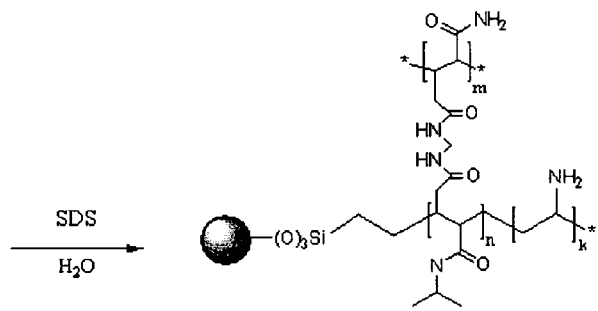

FIG. 20B
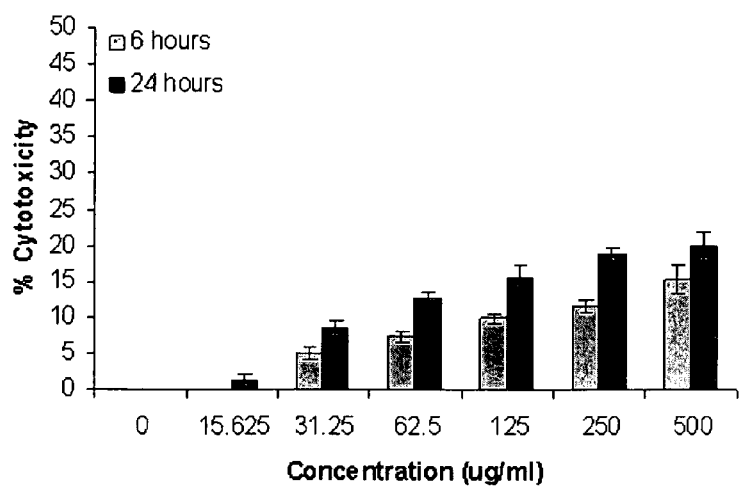
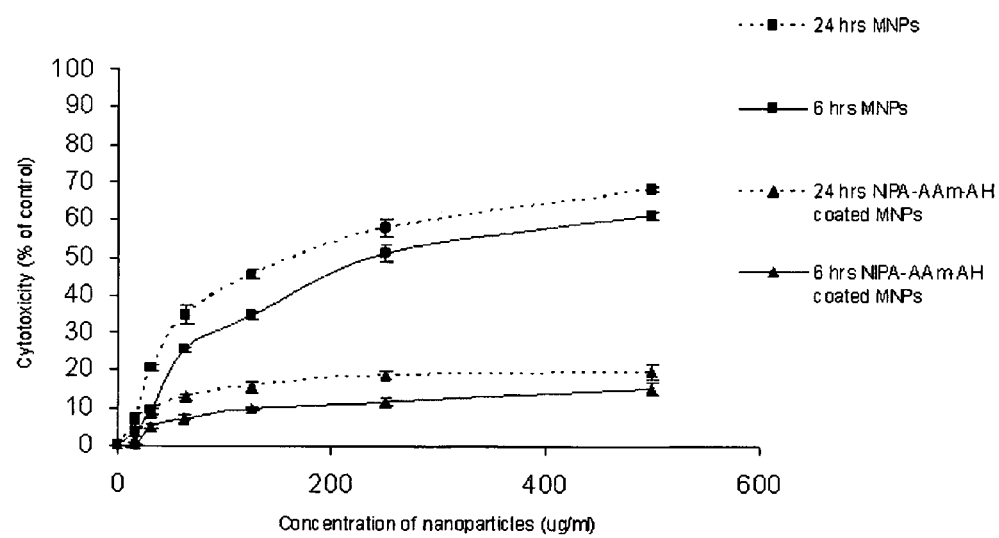
FIG. 20C

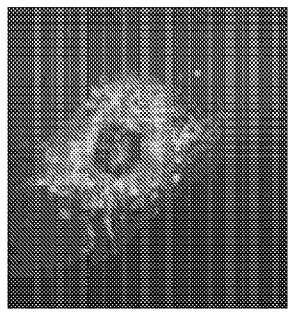 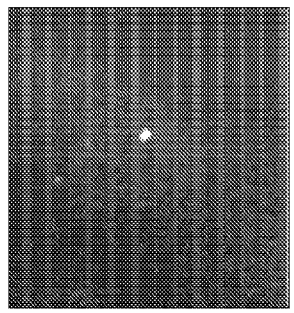 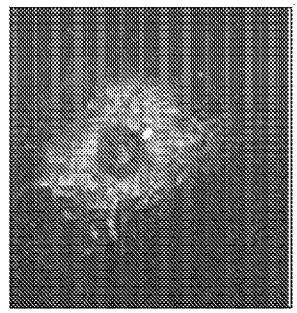
FIG. 32A  FIG. 32B  FIG. 32C
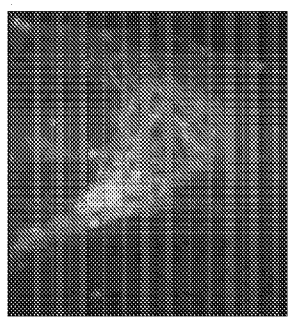 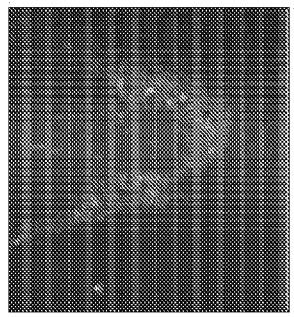 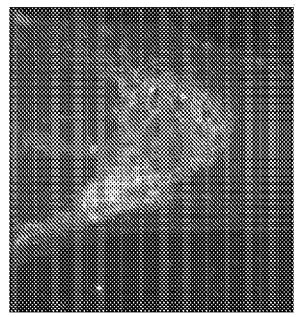
FIG. 33A  FIG. 33B  FIG. 33C
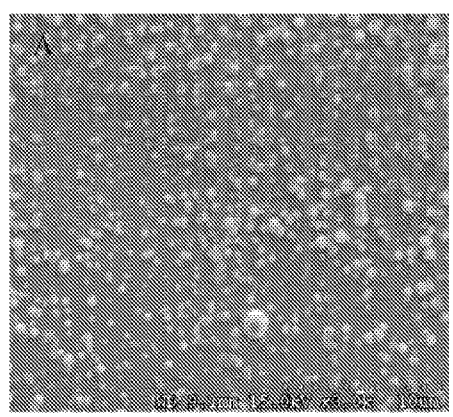 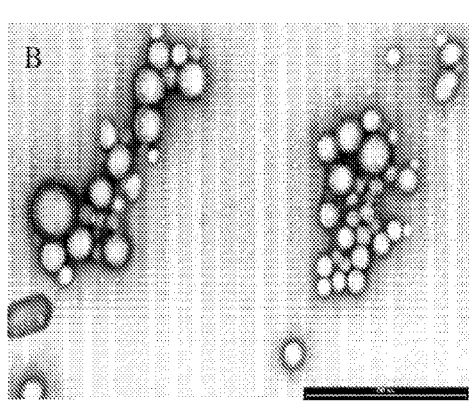
FIG. 35A  FIG. 35B

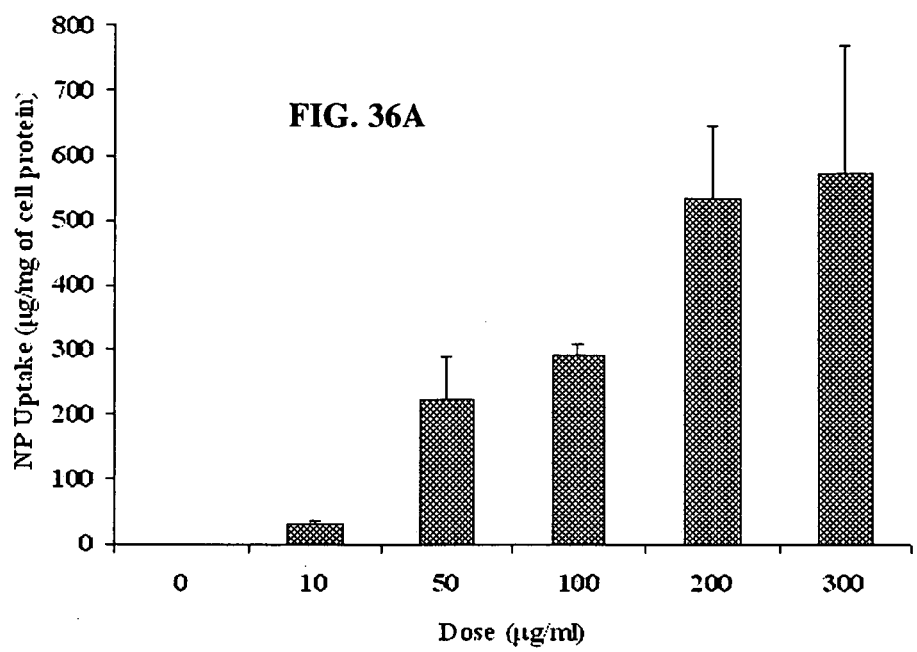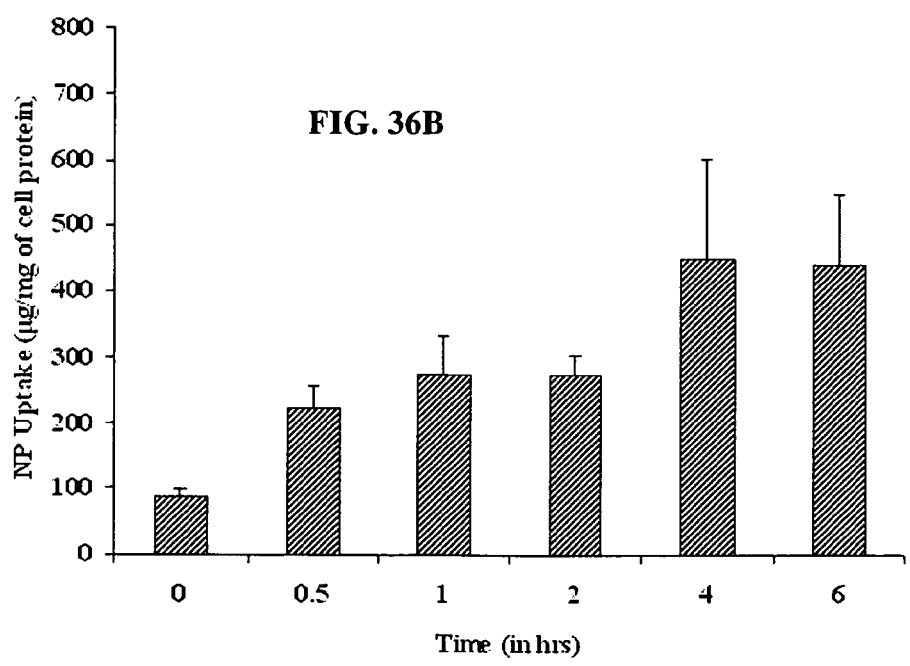

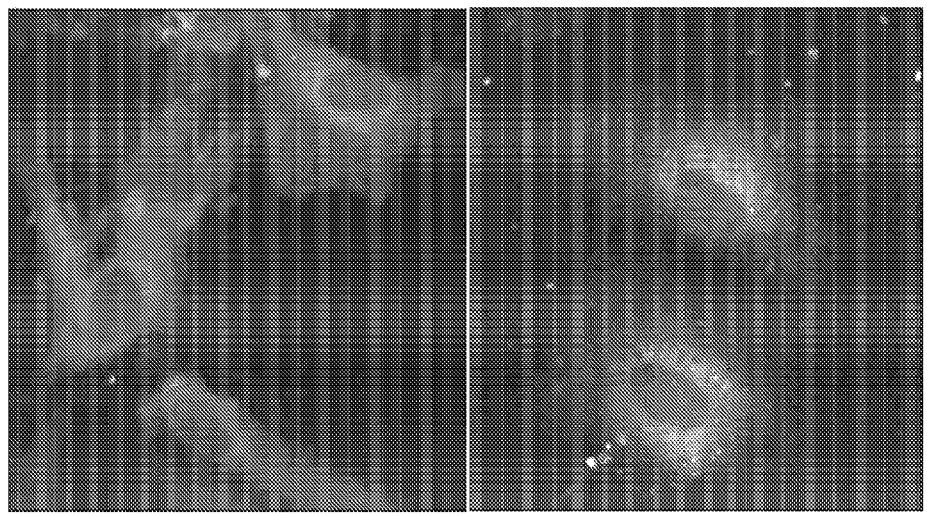
FIG. 37A  FIG. 37B
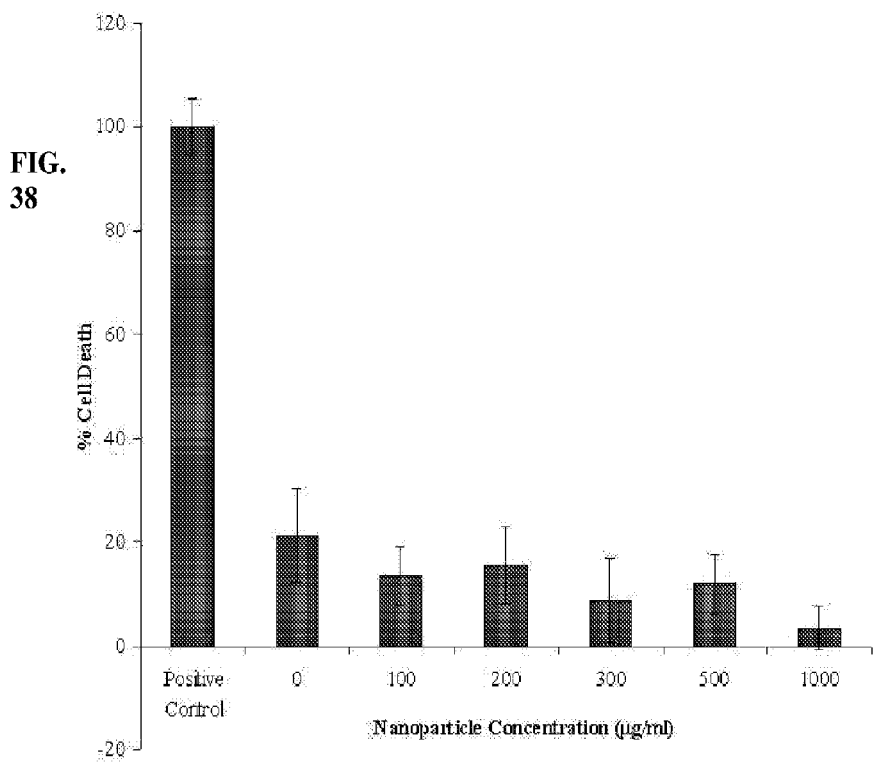
FIG. 38

COMPOSITIONS AND METHODS FOR THERMO-SENSITIVE NANOPARTICLES AND MAGNETIC NANOPARTICLES

STATEMENT OF FEDERALLY SPONSORED RESEARCH AND DEVELOPMENT

This invention was made with government support under HL091232 awarded by the National Institutes of Health and under 0735270N awarded by the American Heart Association. The government has certain rights in the invention.

BACKGROUND OF THE INVENTION

The present invention relates generally to nanoparticles, and more particularly to thermo-sensitive nanoparticles and magnetic nanoparticles. Thermo-sensitive or temperature sensitive polymer nanoparticle have applications in various fields, especially in biotechnology and medicine, including cell culture, tissue engineering, wound healing, and drug delivery systems. For instance, temperature sensitive nanoparticles have been developed as controlled release drug delivery carriers used in cancer treatment and gene therapy. A major advantage of the temperature sensitive nanoparticles as a drug delivery system is their phase change due to temperature. Temperature sensitive polymers undergo a reversible phase transition at a lower critical solution temperature ("LCST"), where the hydrogel hydrophobically collapses and squeezes water out in an entropically favored fashion. A reversible swelling and shrinking behavior based on this phenomenon has been used as a means to control loading and releasing of various therapeutic agents. For example, drugs can be loaded in these nanoparticles at temperatures below the LCST.

A variety of polymers have been used to produce the temperature sensitive nanoparticles as drug delivery systems, although it is difficult to incorporate other molecules such as antibodies and proteins onto temperature sensitive nanoparticles to increase their targeted capabilities. With these nanoparticles, conjugation is possible by performing additional synthetic steps which would introduce impurities altering the LCST significantly. Consequently, there is a need to introduce another monomer to the copolymer of N-isopropylacrylamide (NIPA) and acrylamide (AAm) to functionalize the nanoparticles without changing its LCST dramatically.

Polymeric magnetic nanoparticles (PMNPs) have been developed over many decades for use in several applications such as cell separation, DNA/RNA purification, immunoassays, contrast agents in magnetic resonance imaging (MRI), magnetic targeted drug carriers, tissue engineering, and hyperthermia treatments for cancer. These nanoparticles contain core-shell structures with the core made of magnetic materials and the shell made of either natural or synthetic polymers. Natural polymers such as albumin, cellulose, pullulan, and chitosan, as well as synthetic polymers like polystyrene, poly acrylamide, and poly(L-lactic-co-glycolic) acid have been used to coat magnetic nanoparticles; however the coatings are ineffective and not biocompatible. The embodiments disclosed herein solve these problems as well as others.

SUMMARY OF THE INVENTION

Provided herein are systems, methods and compositions for polymer nanoparticles and polymer magnetic nanoparticles. The advantages of the methods, compositions, and systems will be realized and attained by means of the elements and combinations particularly pointed out in the appended claims.

BRIEF DESCRIPTION OF THE FIGURES

FIG. 5B is a $^{13}$C NMR spectra of NIPA-AAm-AH nanoparticles.

FIG. 12C is the immobilization of NIPA, AAm, and AH on magnetic nanoparticle surface.

FIG. 20B is a graph of the cytotoxicity of functionalized copolymer magnetic nanoparticles; and FIG. 20C is a graph of the cytotoxicity of magnetic nanoparticles (MNPs) and the functionalized copolymer magnetic nanoparticles (NIPA-AAm-AH coated MNPs), where the cells were treated with 1% Triton X-100 used a positive control (100% cytotoxicity)

FIG. 22A is the flow at different flow rates without magnetic field and cells; FIG. 22B is the flow at different shear stress with magnetic filed and without cells; the flow at different shear stress with magnetic field using FIG. 22C endothelial cells, FIG. 22D smooth muscle cells, and FIG. 22E cancer cells.

FIG. 23A is the detection of Texas Red conjugated nanoparticles within the cells, FIG. 23B is the detection of the nucleus (DAPI), and FIG. 23C is the superimposed image of FIGS. 23A and 23B.

FIGS. 32A-C are confocal images of the cellular uptake of control polystyrene nanoparticles in activated ECs under shear stress, where 32A-C represent the plasma membranes were dyed using Texas Red® and imaged using a RITC filter, fluorescent nanoparticles were imaged using a FITC filter, and RITC and FITC overlay, respectively.

FIGS. 33A-C are confocal images of the cellular uptake of GP Ibα polystyrene nanoparticles in activated ECs under shear stress, where 33A-C represent the plasma membranes were dyed using Texas Red® and imaged using a RITC filter, fluorescent nanoparticles were imaged using a FITC filter, and RITC and FITC overlay, respectively.

FIG. 35A is an SEM Image of PLGA nanoparticles; FIG. 35B is a TEM image of PLGA nanoparticles.

FIG. 36A is a graph of the effects of concentrations on the cellular uptake of PLGA nanoparticles in ECs, where the values were obtained after one hour of incubation with nanoparticle solutions and represent mean±SD (n=4); and FIG. 36B is a graph of the effects of the incubation time on the cellular uptake of PLGA nanoparticles in ECs, where the samples were incubated with 100 µg/ml of nanoparticle solution and the values represent mean±SD (n=4).

FIGS. 37A-B are a confocal images of the nanoparticle uptake in ECs, where the plasma membranes were dyed using Texas Red® and imaged using a RITC filter, the fluorescent nanoparticles were imaged using a FITC filter, and confocal images represent an overlay of RITC and FITC filters and were taken at Ex($\lambda$) 488 nm, Em($\lambda$) 543 nm; where FIG. 37A is the overlay confocal image of the control cells while FIG. 37B is the overlay confocal image of the nanoparticle uptake by EC's at a concentration of 200 µg/ml.

FIG. 38 is a graph of the cytotoxicity of the PLGA nanoparticles.

DETAILED DESCRIPTION OF THE PREFERRED EMBODIMENTS

Figure 1A:
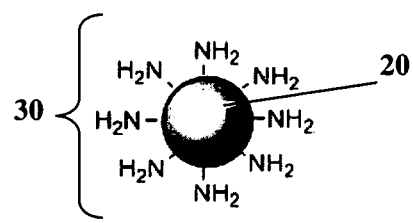
FIG. 1A is the structure of one embodiment of the functionalized copolymer nanoparticle.
Figure 1B:
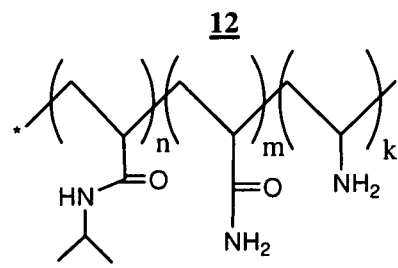
FIG. 1B is the structure of the monomer unit 12.

Generally speaking, a temperature sensitive nanoparticle comprises a lower critical solution temperature ("LCST") that is above body temperature (~36.8-37.5° C.) and can be incorporated with various molecules at the surface of the nanoparticle. At or above the LCST, the temperature sensitive nanoparticles hydrophobically collapse and expel water in an entropically favored fashion, i.e. swelling and shrinking events. The synthetic polymer poly N-isopropylacrylamide ("NIPA") is capable of undergoing reversible swelling and shrinking events at a LCST of 34° C. The reversible swelling and shrinking events may be used for controlled drug delivery in response to changes in temperature. In one embodiment, block copolymers containing NIPA and co-acrylamide ("AAm") interpenetrating networks have a LCST above body temperature. A representative temperature sensitive nanoparticle comprising the functionalized co-polymer nanoparticles 10 is shown in FIG. 1A. The functionalized copolymer nanoparticles 10 include a plurality of functionalized co-polymer repeating units 12 of poly(N-isopropylacrylamide-co-acrylamide-co-allylamine) ("NIPA-AAm-AH"), as shown in FIG. 1B, where n is from 1 to 12, m is from 1 to 12, and k is from 1 to 12. The copolymer repeating units 12 can be a different order, combination, or number or repeating units, i.e. NIPA-NIPA-AAm-AH, NIPA-AAm-AAm-AH, NIPA-AAm-AH-AH, AAm-NIPA-NIPA-AH, or AH-AAm-NIPA-AH etc. and the like, whilst maintaining a LCST above body temperature. The copolymer repeating units 12 may include a ratio of NIPA to AAm to AH, i.e. the ratio of the monomers in the repeating units 12 can be changed with respect to keep the LCST above body temperature. Alternatively, the monomers in the repeating units 12 can be included in the functionalized copolymer nanoparticle by a % mole as to provide an LCST above body temperature. In one embodiment, NIPA is present at about 58% mole, AAm is present at about 12% mole, and AH is present at about 30% mole, which results in a ratio of 4.83:1:2.5 of NIPA to AAm to AH. Alternatively, the NIPA is present in the functionalized copolymer nanoparticle in the range of about 35-75% mole, preferably between about 45-65% mole, or preferably between 50-60% mole. Alternatively AAm is present in the functionalized copolymer in the range of about 1-20% mole, preferably between about 5-15% mole, and most preferably between about 9-13% mole. Alternatively, AH is present in the functionalized copolymer nanoparticle between about 10-40% mole, preferably between about 20-35% mole, or preferably between about 25-32% mole, where % mole is the mole of the polymer over the overall mole times 100%.

As shown in FIG. 1A, the functionalized copolymer nanoparticles include a core 20 and an outer surface 30. The core 20 includes the plurality of co-polymer repeating units 12 in an intertwined mesh polymer network, whereby the co-polymer repeating units 12 includes weak interactions between adjacent and intertwined co-polymer repeating units 12. The outer surface 30 includes a plurality of functional groups from the AH monomer. In one embodiment, the functionalized copolymer nanoparticles 10 are synthesized through a free radical polymerization method, where NIPA is polymerized with AAm and AH to increase the LCST and to provide amine groups on the outer surface 30 functionalization, respectively. "Functionalization" is the inclusion of functional groups for conjugation of biomolecules, bioactive molecules such as antibodies and specific ligands, and the like. Polymerization of NIPA with allylamine does not significantly alter the LCST of the NIPA polymer. In one embodiment, the functional groups include amine groups for conjugation. The functionalized copolymer nanoparticles 10 could be used in targeted and controlled drug delivery and tissue engineering applications.

Alternatives for allylamine include allylamine derivatives and analogs that maintain the LCST of the nanoparticle above body temperature. Allylamine derivatives and analogs may include an alkyl group with an amine, which may be a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The functional groups may be atoms or groups of atoms that are capable of further chemical reactivity such as reacting with a ligand or antibody to attach the ligand or antibody to the temperature sensitive nanoparticles, or to bind a molecule of interest. Different functional groups would affect the LCST, and when different functional groups are used, the LCST of the nanoparticle must be maintained or adjusted to be above body temperature. For example, the functional group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol, as described below.

In one embodiment, the functionalized copolymer nanoparticles 10 include a size inversely proportional to the surfactant concentrations used in the synthesis methods. The size of the functionalized copolymer nanoparticles 10 may include an average size between about 2 and about 900 nm, preferably nanoparticles having an average size between about 70 and about 700 nm, and most preferably, the nanoparticles have an average size between about 80 and about 500 nm. The shape of the functionalized copolymer nanoparticles 10 may include a spherical, round, cubodial, or polygonal shape. Functionalized copolymer nanoparticles 10 are biocompatible and do not have significant cytotoxicity activity against human cells. Finally, the functionalized copolymer nanoparticles 10 include a drug release profile at different temperatures. In one embodiment, more drugs or bioactive molecules may be released from the functionalized copolymer nanoparticles 10 at an LCST of 41° C. compared to that of 37° C. and 4° C. Most preferably, the LCST is above body temperature at least about 37-45° C., preferably between at least about 38-43° C., most preferably between at least about 40-42° C.

In one embodiment, the synthesis of the functionalized copolymer nanoparticles 10 comprises the polymerization of poly(N-isopropylacrylamide-co-acrylamide-co-allylamine) including N,N'-methylenebisacrylamide (BIS) as the cross-linking agent, sodium dodecyl sulfate (SDS) as the surfactant, and ammonium persulfate (APS) and N,N,N',N'-tetramethyl ethylene diamine (TEMED) as a pair of redox initiators in de-ionized water at room temperature. Redox initiators or radical initiators are substances that can produce radical species under mild conditions and promote radical polymerization reactions. Alternative redox initiators may be used, including, but not limited to halogen molecules, azo compounds, and organic peroxides. Surfactants are wetting agents that lower the surface tension of a liquid, allowing easier spreading, and lower the interfacial tension between two liquids. Alternative surfactants may be used, such as ionic anionic, cationic, or zwitterionic molecules, or nonionic molecules, Tweens, or Pluronics. Alternative cross linking agents may include derivatives of methylenebisacrylamide, N,N-(1, 2-dihydroxyethylene)bisacrylamide, derivatives of ethylene glycol di(meth)acrylate, and the like.

In one embodiment, 1.108 g of NIPA, 0.143 g of acrylamide (AAm), 378 μL of allylamine hydrochloric acid (AH), and 0.0262 g of BIS are dissolved in 100 ml of de-ionized water. The amount of NIPA, AAm, and AH used in the starting materials determine the % mole composition for NIPA, AAm, and AH in the final polymerized product. AH does not change the LCST and is only needed enough to just coat the surface with antibody, so the percentage of AH can be changed according to preferences for functionalizing the functionalized copolymer nanoparticles. SDS is added to the solution at various concentrations (1.53, 0.298, 0.198, and 0.0243 mM) under continuous stirring. The solution is then purged with Argon for 30 minutes. Then, 0.078 g of APS and 101 μL of TEMED are added to the solution and the reaction was carried out at room temperature under Argon for 2 hours. After the reaction was completed, the functionalized copolymer nanoparticles were dialyzed against de-ionized water using 10 kDa molecular weight cut off for 3 days to remove surfactants and un-reacted materials.

Figure 2:
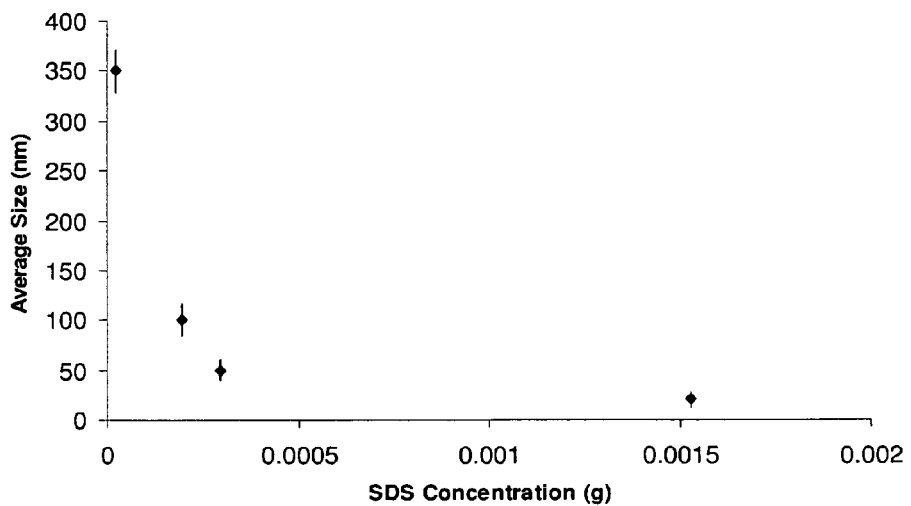
FIG. 2 is a graph of the effect of SDS concentrations on the mean size of the functionalized copolymer nanoparticles (the result is represented as mean±S.D., n=3).

The measurement of the average diameter of the functionalized copolymer nanoparticles may be performed in de-ionized water at room temperature ~25° C. by dynamic light scattering technology (Nanotrac 150, Microtrac. Inc.). As shown in FIG. 2, different concentrations of the surfactant (SDS) may be used to synthesize nanoparticles with various sizes, and the size of the functionalized copolymer nanoparticles increases as the concentration of SDS decreases. In one embodiment, the size of the functionalized copolymer nanoparticles is inversely proportional to the concentration of SDS, and this type of relationship between surfactants and the nanoparticle size is nonlinear at SDS concentrations higher than 0.298 mM.

Figure 1C:
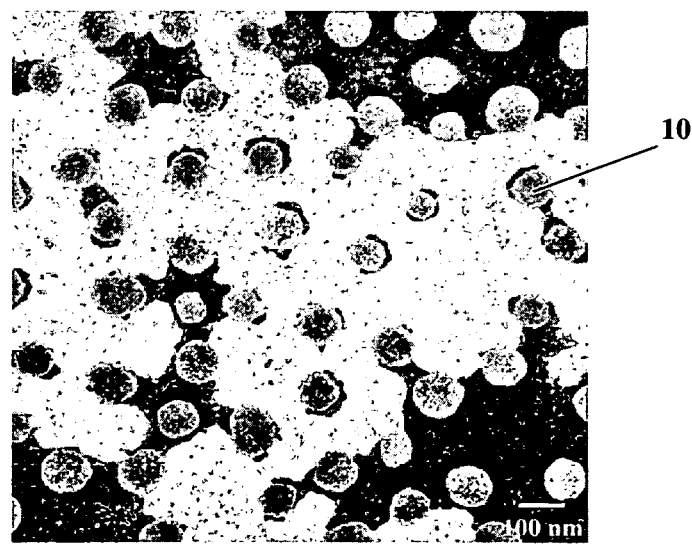
FIG. 1C is a TEM image of the functionalized copolymer nanoparticle.
Figure 3:
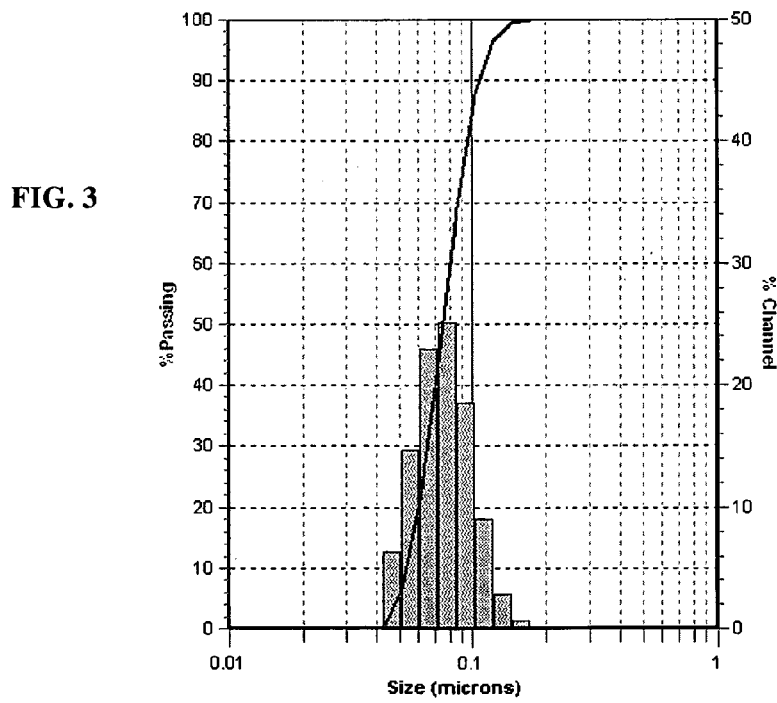
FIG. 3 is a graph of the particle size distribution of 100-nm functionalized copolymer nanoparticles.

Several characterization techniques may be performed for 100-nm size functionalized copolymer nanoparticles. As shown in FIG. 3, the nanoparticle size distribution of 100 nm particles is shown, where the functionalized copolymer nanoparticles range from about 60-200 nm. The size and shape of the functionalized copolymer nanoparticles may be analyzed using Transmission Electron Microscope (TEM, JEOL 1200 EX)), as shown in FIG. 1C. In general, samples are prepared by drop casting an aqueous dispersion of the functionalized copolymer nanoparticles onto a carbon coated copper grid. The grid is then dried at room temperature before viewing under the microscope. The nanoparticles are stained with phosphotungstic acid (PTA) at a concentration of 0.01 wt % before observation. As shown in FIG. 1C, the black background around the nanoparticles is the phosphotungstic acid stain that is used to define the outer edge of the nanoparticles. TEM revealed that the preparation procedure results in spherical nanoparticles. The size noted by TEM is within the size measured by Nanotrac.

Figure 4:
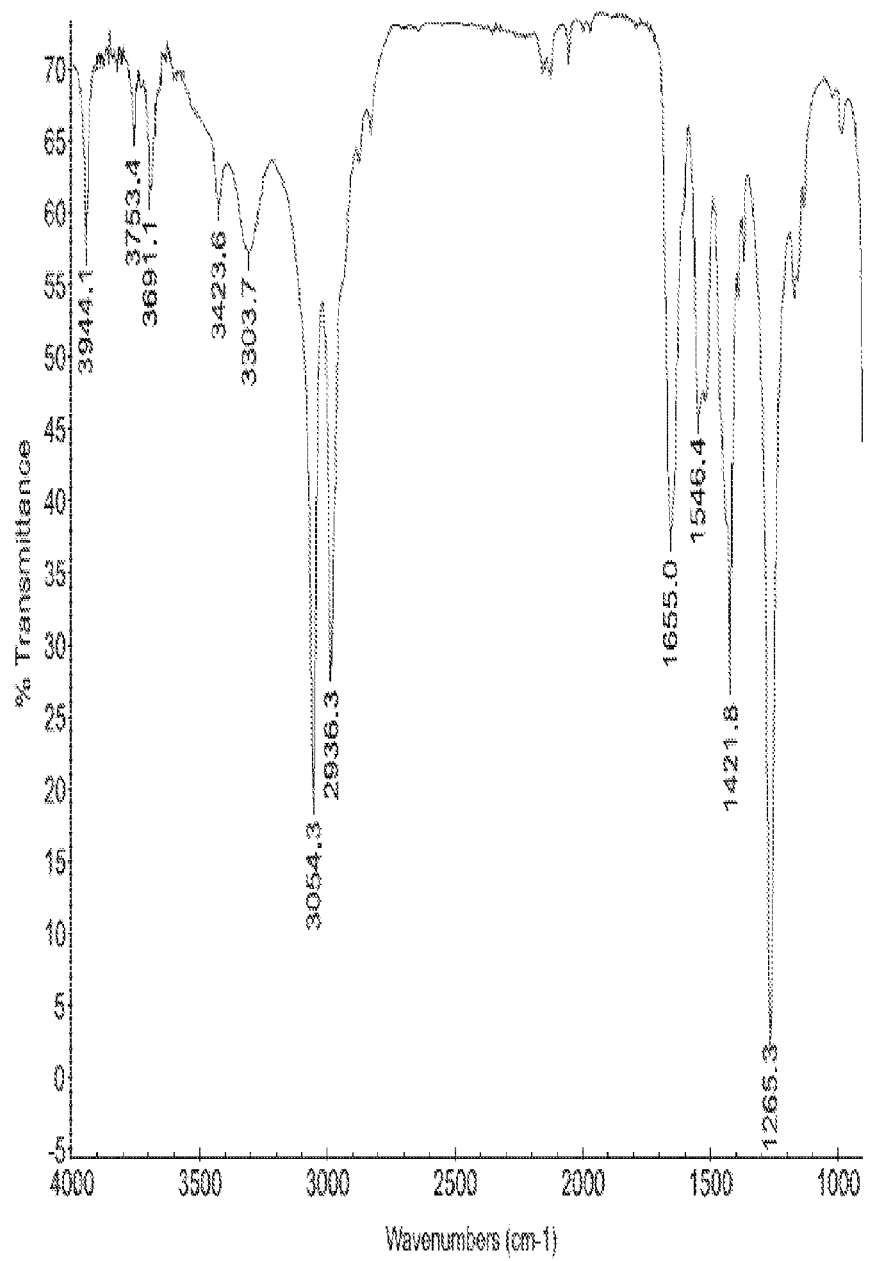
FIG. 4 is a FTIR spectrum of the functionalized copolymer nanoparticle at room temperature (25° C.) showing the chemical composition analysis of the nanoparticle.

The chemical composition of the synthesized functionalized copolymer nanoparticles may be analyzed using both Fourier Transform Infrared Spectroscopy (FTIR) and nuclear magnetic resonance (NMR). Dried samples of functionalized copolymer nanoparticles may be dissolved in dichloromethane and a drop of the dissolved solution may be placed on NaCl discs. FTIR spectra may be recorded in the transmission mode using a Thermo FT-IR Nicolet-6700. The spectrum taken may range from 4000 to 400 $cm^{-1}$. As shown in FIG. 4, the stretching vibration for FTIR appearing in the range of 2900-3100 $cm^{-1}$ corresponds to C—H bands. The IR peak at 3423.6 $cm^{-1}$ corresponds to the stretching vibration of the primary amine group in the functionalized copolymer nanoparticles. The peak from the secondary amine group of NIPA is observed around 3308.7 $cm^{-1}$. Furthermore, the carbonyl group of NIPA and AAm is observed at 1655 $cm^{-1}$. These peaks indicate that the NIPA-AAm-AH nanoparticle comprise of functional groups corresponding to their constitute monomers, as shown in FIG. 1B.

Figure 5A:
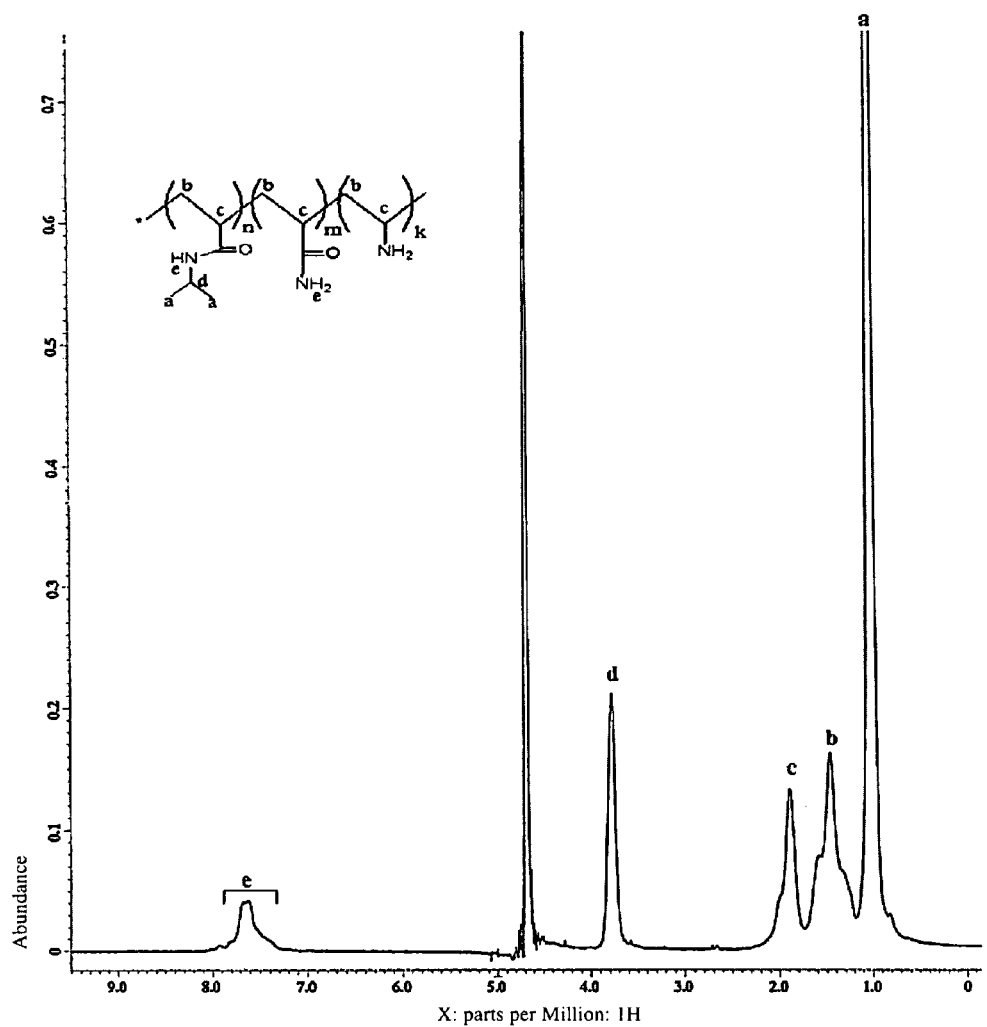
FIG. 5A is $^1$H NMR spectra of the functionalized copolymer nanoparticles.

In order to analyze the chemical composition of the functionalized copolymer nanoparticle in more detail, proton ($^1$H NMR) and carbon nuclear magnetic resonance ($^{13}$C NMR) may be used. $^1$H NMR and $^{13}$C NMR spectra may be recorded at 25° C. on 300 and 500 MHz spectrometers, respectively. Chemical shifts may be measured relative to residual non-deuterated solvent resonances. The spectrum of the functionalized copolymer nanoparticles may be recorded in a deuterated dimethyl sulfoxide (DMSO) solution. As shown in FIG. 5A, in $^1$H NMR, the backbone hydrogen of the functionalized copolymer nanoparticle is observed at 1.89 (c, broad, 1H) and 1.46 (b, broad, 2H). The hydrogen attached to the isopropyl of NIPA is observed at 3.78 (d, multiplet, 1H), and the hydrogen of methyl groups in NIPA is observed at 1.02 (a, multiplet, 6H). The broad peak at 7.40 to 7.80 ppm is from the hydrogen in the amide groups. As shown in FIG. 5B, the $^{13}$C NMR identified the carbonyl group of AAm at 177.98 ppm and the carbonyl group of NIPA at 173.96 ppm. Furthermore, the composition of the functionalized copolymer nanoparticle may be determined by using $^{13}$C NMR and titration. As shown in Table 1, the composition of the functionalized copolymer nanoparticle is approximately close to those in the feed (i.e. the original amounts of materials), implying that polymerization of the functionalized copolymer nanoparticle was as expected.

TABLE 1

Monomer ratio in the feed and in the functionalized copolymer nanoparticle predicted by NMR and titration

| Molecule | In the feed ×10$^{-3}$ mole | In the NIPA-AAm-AH % mole |
|---|---|---|
| NIPA | 9.79 (58%) | 61.9% |
| AAm | 2.00 (12%) | 9.8% |
| AH | 5.05 (30%) | 28.3% |

Figure 6:
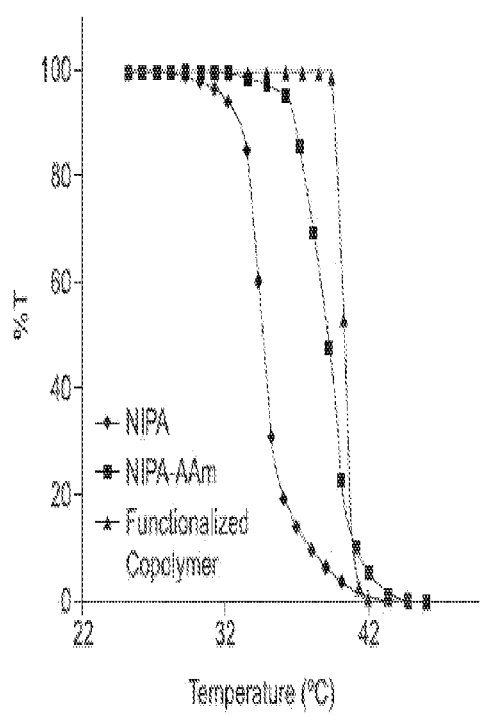
FIG. 6 is a graph of LCST of NIPA, NIPA-AAm, and the functionalized copolymer nanoparticles measured by using UV-Vis. Spectrophotometer.
Figure 7A:
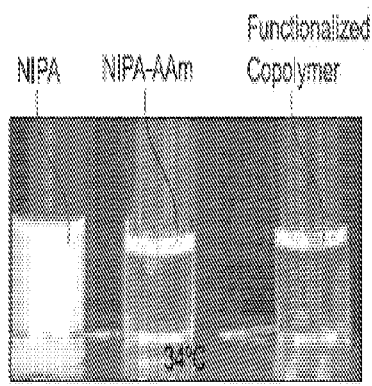
FIGS. 7A-C are photographs of NIPA, NIPA-AAm, and the functionalized copolymer nanoparticles at different temperatures, where the nanoparticles were placed (FIG. 7A) at 34° C., (FIG. 7B) at 39° C., and (FIG. 7C) at 40° C., and a color change was observed when the phase transition occurred.
Figure 7B:
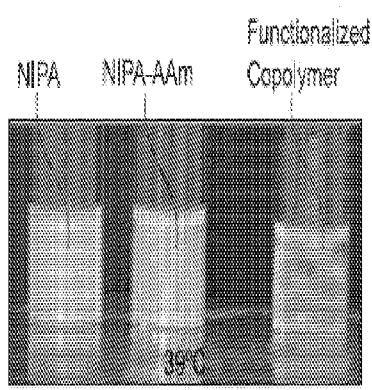
Figure 7C:
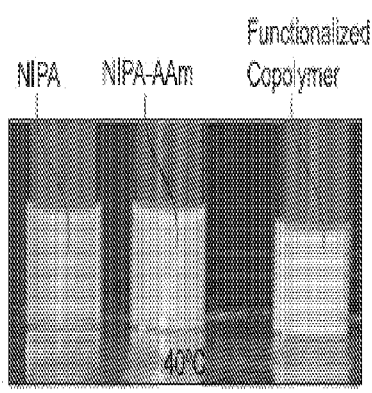

To determine the temperature at which the phase transition occurs in the nanoparticles, i.e. the LCST, a UV-Vis spectrophotometer may be used. Optical transmittance of the aqueous nanoparticle solution (2 mg/ml) at various temperatures (25-45° C. with 1° C. intervals) may be measured at 650 nm with a UV-Vis spectrophotometer (Cary 50 UV-Vis spectrophotometer coupled with PCB-150 circulating water bath). As shown in FIG. 6, the LCST of NIPA nanoparticles is 34° C. The rate at which the transition occurs slowly changes around 32° C., and then the intensity sharply decreases at 34° C. Also shown in FIG. 6, the phase transition of NIPA-AAm and NIPA-AAm-AH nanoparticles occurs sharply at 39° C. and 40° C., respectively. In addition to the LCST measurements, the phase transition of the functionalized copolymer nanoparticles can be seen when the solution goes from clear to cloudy at each specific LCST, as shown in FIGS. 7A-C. FIGS. 7A-C are photographs of NIPA, NIPA-AAm, and the functionalized copolymer nanoparticles, respectively, at different temperatures, where the nanoparticles were placed (FIG. 7A) at 34° C., (FIG. 7B) at 39° C., and (FIG. 7C) at 40° C., and a color change (clear to cloudy) was observed when the phase transition occurred.

Figure 8:
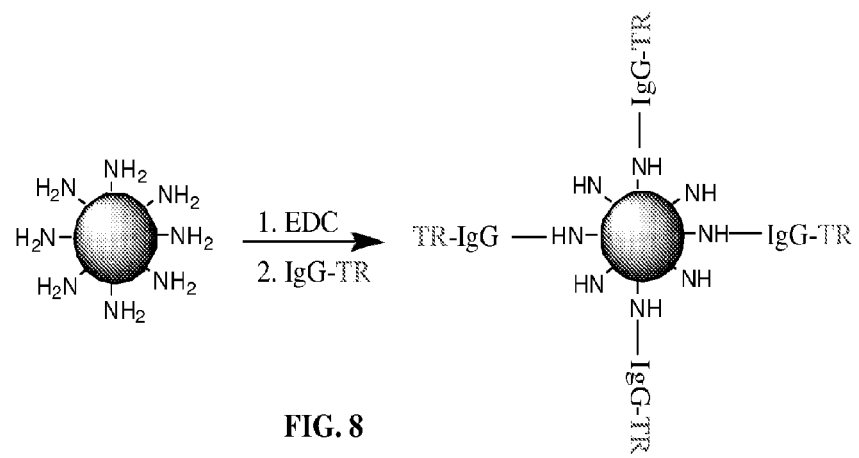
FIG. 8 is a schematic diagram of the conjugation reaction of the functionalized copolymer nanoparticles with IgG-TR.
Figure 9A:
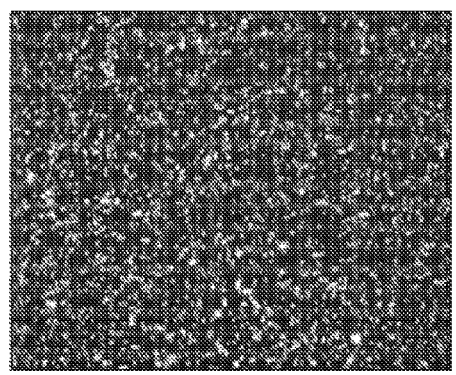
FIG. 9A is a phase contrast microscopy image of NIPA-AAm nanoparticles reacted with fluorescent IgG.
Figure 9B:
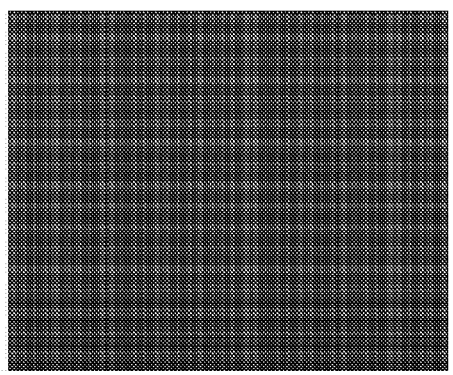
FIG. 9B is a fluorescent microscopy images of NIPA-AAm reacted with fluorescent IgG.
Figure 9C:
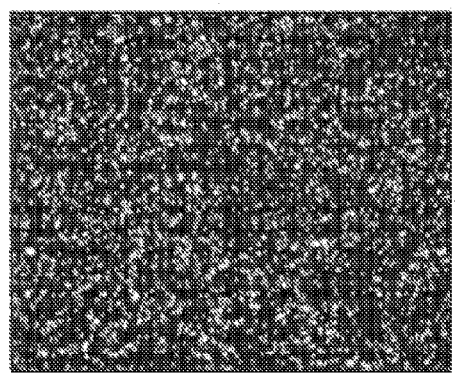
FIG. 9C is a phase contrast microscopy image of the functionalized copolymer nanoparticles reacted with fluorescent IgG.
Figure 9D:
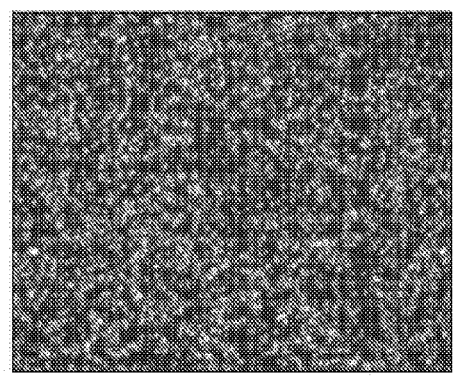
FIG. 9D is a fluorescent microscopy image of the functionalized copolymer reacted with fluorescent IgG.

In order to test the conjugation or functionalization capability of the functionalized copolymer nanoparticles, Bovine anti-rabbit IgG-Texas Red (IgG-TR) may be used. Alternative functionalization steps are provided in the Examples section. The IgG-TR fluorescent antibodies are conjugated onto the NIPA-AAm-AH nanoparticle surfaces via carbodiimide chemistry, as shown in FIG. 8A. In one embodiment, 0.01 g of the functionalized copolymer nanoparticles is dissolved in 0.5 ml of 2-(N-Morpholino)ethanesulfonic acid sodium salt (MES) (0.1 M) buffer solution containing 0.01 g of N-(3-dimethylaminopropyl)-N'-ethylcarbodiimide hydrochloride (EDC). The reaction is mixed well for 10 minutes at room temperature and 0.2 mg of IgG-TR is added to the above solution and allowed to react with the functionalized copolymer nanoparticles for 2 hours at room temperature under stirring and dark conditions. The nanoparticle solution is dialyzed under dark conditions molecular weight cutoff (MWCO) of 100 kDa against DI-$H_2O$ for 1 week to remove unreacted IgG-TR. The sample is lyophilized and resuspended in 50% glycerol in water before imaging by an enhanced optical fluorescent microscope (Cytoviva). As shown in FIG. 9D, a bright red color was observed in the functionalized copolymer nanoparticles, whereas this fluorescence was not seen in NIPA-AAm nanoparticles (control), as shown in FIG. 9B, which indicate that the functionalized copolymer nanoparticles have amine functional groups available which can be utilized for conjugation of other molecules.

Figure 10:
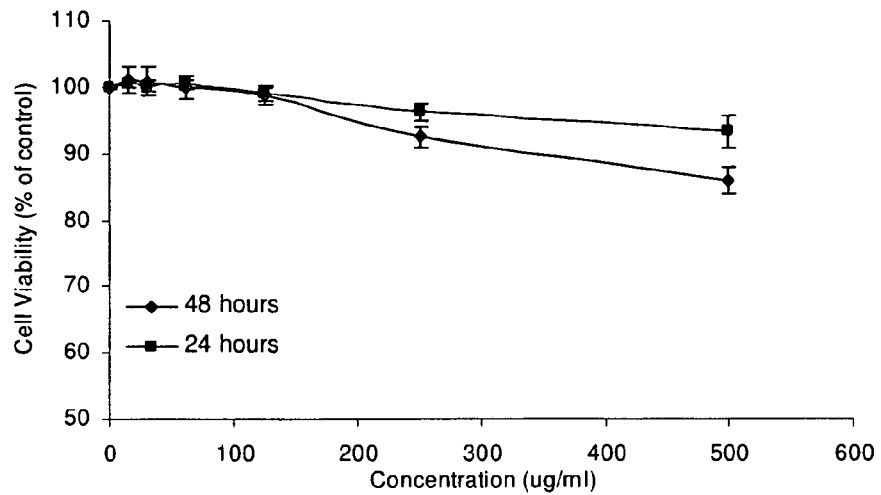
FIG. 10 is a graph of the cell viability of 3T3 fibroblast cells after 24 and 48 hours exposure to nanoparticles at various concentrations, where the cell viability was assessed using MTS assays and cells without exposure to nanoparticles served as controls.

Cytotoxicity studies may be carried out on human 3T3 fibroblast cells (NIH) using (3-(4,5-dimethylthiazol-2-yl)-5-(3-carboxymethoxyphenyl)-2-(4-sulfophenyl)-2H-tetrazolium (MTS) assays (Promega). The MTS assay is based on the competence of the live cells to reduce the MTS into formazan. In order to investigate the biocompatibility of the functionalized copolymer nanoparticles, the cell viability of 3T3 fibroblast cells may be studied. The 3T3 fibroblast cells were incubated with synthesized functionalized copolymer nanoparticles at various concentrations (16, 31, 62, 125, 250, and 500 µg/ml). The cell viability was determined after 24 and 48 hours of incubation with the functionalized copolymer nanoparticles. The cytotoxicity results are presented as the percentage of viable cells in each sample in comparison to controls (cells not treated with the nanoparticles). As shown in FIG. 10, there is no significant difference in the cell viability between control cells and cells exposed to the functionalized copolymer nanoparticles, especially at concentrations less than 250 µg/ml. For all concentrations, the values of the cell toxicity are less than 15% at both time points, which indicate that the synthesized functionalized copolymer nanoparticles exhibit low cytotoxicity, satisfying criteria for a new drug delivery system.

For drug loading and release studies, a cancer drug, doxorubicin ("DOX"), was used. Alternatively, any pharmacologically active or therapeutic agent may be loaded into the functionalized copolymer nanoparticles selected from the group of antibiotic drugs, antiviral drugs, anti-cancer drugs, chemotherapy drugs, neoplastic agents, steroids, anti-clotting drugs, aspirin, antiproliferative agents, antioxidants, antimetabolites, non-steroidal and steroidal anti-inflammatory drugs, immunosuppressants, genetic materials including DNA and RNA fragments for gene delivery, antibodies, lymphokines, growth factors, radionuclides, and the like.

In one embodiment, 10 mg of lyophilized functionalized copolymer nanoparticles and 5 mg of DOX dispersed in a phosphate buffer solution (PBS). DOX may be added as the water soluble form of Adriamycine at an optimal percentage % w/v. The PBS solution is stirred at 4° C. for 3 days to allow DOX to entrap within the functionalized copolymer nanoparticles. The functionalized copolymer nanoparticle solution is then dialyzed against PBS for 3 hours to remove the free DOX not entrapped with the functionalized copolymer nanoparticles. The time to remove free DOX may be predetermined for optimal separation of the unencapsulated drug. The dialysate is then analyzed using an Infinite M200 plate reader (Tecan) in order to determine the amount of DOX in the dialysate ($\lambda_{ex}$ 470 nm and $\lambda_{em}$ 585 nm). This value was then compared with the total amount of DOX to determine the DOX loading efficiency of the functionalized copolymer nanoparticles. Loading efficiency was calculated according to the Equation (1):

$$\% \text{ Loading Efficiency} = \frac{\text{total [DRUG] used} - \text{[DRUG] present in dialysate}}{\text{total [DRUG] used}} \times 100\% \quad (1)$$

The drug release profile of the synthesized nanoparticles may be determined by placing, 2 ml of the drug loaded nanoparticle solution inside dialysis bags with a MWCO of 10,000 Da. Samples are then dialyzed against PBS at 4° C., 37° C., and 41° C. At designated time intervals, 1 ml of dialysate was removed from each sample and stored at −20° C. for later analysis. The dialysate volume was reconstituted by adding 1 ml of fresh PBS to each sample. After experiments, the dialysate samples were analyzed using an Infinite M200 plate reader ($\lambda_{ex}$ 470 nm and $\lambda_{em}$ 585 nm) to quantify the amount of DOX released.

Figure 11A:
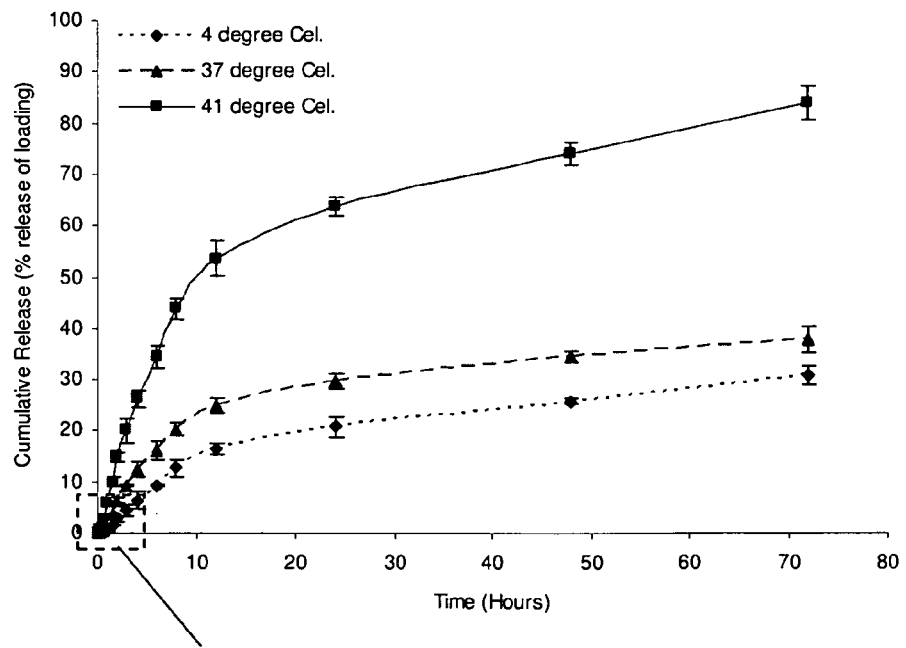
FIG. 11A is a graph of in vitro release profiles of DOX at 40° C., 370° C., and 410° C. over 72 hours.
Figure 11B:
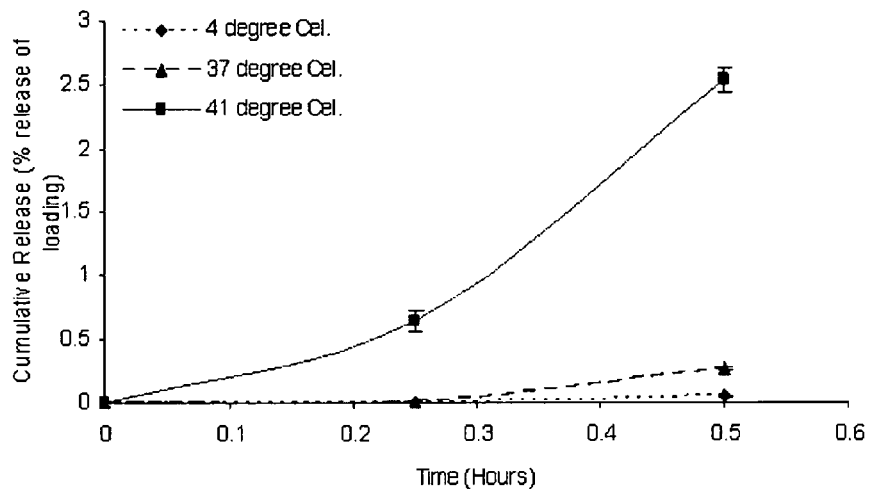
FIG. 11B is an exploded view of the graph along box A and shows the cumulative percent release of DOX over 30 minutes.

Using DOX as a model drug, approximately 66% of the incubated DOX was loaded into the functionalized copolymer nanoparticles. In addition, the cumulative percent release of DOX at 41° C. was significantly higher than at 37° C. and 4° C., as shown in FIG. 11A, which indicates that the functionalized copolymer nanoparticles are temperature sensitive polymers whereby the nanoparticles collapse upon themselves and squeeze the drug out at its LCST. After 72 hours, 84% of the encapsulated DOX was released at 41° C., whereas at 37° C. and 4° C. approximately 31% and 38%, respectively, were released. The drug release profile of the DOX over the first 30 minutes is also shown in FIG. 11B. After 30 minutes, the cumulative percent release of DOX is only 0.045% and 0.27% at 4° C. and 37° C., respectively, whereas at 41° C. it is 2.5%.

The targeting capability of the synthesized functionalized copolymer nanoparticles and the pharmacological effects of drug-loaded and antibody conjugated functionalized copolymer nanoparticles for drug delivery applications may be investigated. The targeting capabilities may be investigated using a flow chamber, an animal vessel, and inside animal body, as described below. The pharmacological effects may be investigated using tissue culture and animal models, as described below.

Temperature Sensitive Functionalized Copolymer Magnetic Nanoparticles

Figure 12A:
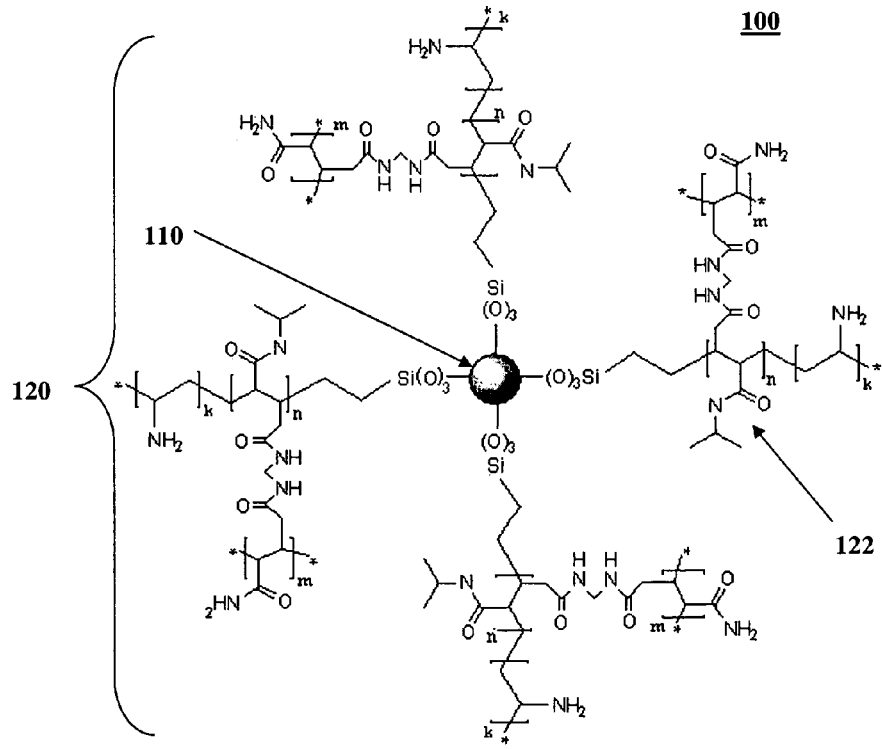
FIG. 12A is a schematic of one embodiment of the functionalized copolymer magnetic nanoparticle.

An alternative embodiment of the temperature sensitive nanoparticle includes a plurality of functionalized copolymer magnetic nanoparticles 100 for controlled drug delivery applications, as shown in FIG. 12A. The functionalized copolymer magnetic nanoparticles 100 comprise a magnetic core 110 with a copolymer shell 120 surrounding the magnetic core 110. In one embodiment, the copolymer shell 120 comprises a plurality of repeating units 122 of N-isopropylacrylamide, acrylamide, and allylamine (NIPA-AAm-AH). "Copolymer" is a polymer comprising of at least two repeating units or monomers 122. Each monomer unit 122 of NIPA-AAm-AH is an additional layer added to the copolymer shell 120, which may increase the thickness of the copolymer shell 120. The copolymer shell 120 includes a weak interaction in the backbone of repeating units, where the backbone of repeating units includes an intertwined or cross-linked structure. The monomer unit 122 is generally shown in FIG. 12A, where n is NIPA and ranges from 1 to 12, m is AAm and ranges from 1 to 12, and k is AH and ranges from 1 to 12. The copolymer repeating units 12 can be in a different order, combination, or number or repeating units, i.e. NIPA-NIPA-AAm-AH, NIPA-AAm-AAm-AH, NIPA-AAm-AH-AH, AAm-NIPA-NIPA-AH, or AH-AAm-NIPA-AH etc. and the like, whilst maintaining a LCST above body temperature. The copolymer repeating units 12 may include a ratio of NIPA to AAm to AH. The ratio of the monomers in the repeating units 12 can be changed with respect to keep the LCST above body temperature. Alternatively, the monomers in the repeating units 12 can be included in the functionalized copolymer nanoparticle by a % mole as to provide an LCST above body temperature. In one embodiment, NIPA is present at about 58% mole, AAm is present at about 12% mole, and AH is present at about 30% mole, which results in a ratio of 4.83: 1:2.5 of NIPA to AAm to AH. Alternatively, the NIPA is present in the functionalized copolymer nanoparticle in the range of about 35-75% mole, preferably between about 45-65% mole, or preferably between 50-60% mole. Alternatively AAm is present in the functionalized copolymer in the range of about 1-20% mole, preferably between about 5-15% mole, and most preferably between about 9-13% mole. Alternatively, AH is present in the functionalized copolymer nanoparticle between about 10-40% mole, preferably between about 20-35% mole, or preferably between about 25-32% mole.

The functionalized copolymer magnetic nanoparticles 100 include a general spherical shape, alternatively, the shape may comprise a general round, cuboidal, or polygonal shape. The magnetic core 110 and the copolymer shell 120 include a general spherical shape, alternatively, the shape may comprise a general round, cuboidal, polygonal shape, or any other shape. The size of the functionalized copolymer magnetic nanoparticles 100 may include an average size between about 2 and about 900 nm, preferably nanoparticles having an average size between about 70 and about 700 nm, and most preferably, the nanoparticles have an average size between about 80 and about 200 nm. The size of the magnetic core 110 may include an average size between about 2-200 nm, preferably between about 4-100 nm, and most preferably between about 6-50 nm. The size of the copolymer coating 120 may include an average size between about 10-800 nm, preferably between about 50-500 nm, and most preferably between about 75-200 nm. The encapsulation thickness of the copolymer shell 120 may be balanced against the magnetic properties to obtain an appropriate magnetic product. Functionalized copolymer magnetic nanoparticles may be encapsulated with different thicknesses of the shell layers by varying the amount of polymers, crosslinkers, and surfactant concentration and water/oil ratio in the synthesis process. Then the aggregation, magnetic properties, the movement and heat generation of these functionalized copolymer magnetic nanoparticles under influence of magnetic fields, are measured to find an optimal thickness value. This optimal thickness value has the least aggregation of nanoparticles and the highest magnetic strength. Alternatively, other energies may heat the magnetic nanoparticles, such as radiowave, optical energy (infrared), & ultrasound.

Alternatives for allylamine include allylamine derivatives and analogs may be used but the LCST must be maintained above body temperature. Allylamine may include an alkyl group, which may be a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The functional groups may be atoms or groups of atoms that are capable of further chemical reactivity such as reacting with a ligand or antibody to attach the ligand or antibody to the temperature sensitive nanoparticles, or to bind a molecule of interest. Different functional groups would affect the LCST, and when different functional groups are used, the LCST must be maintained/adjusted at above body temperature. For example, the functional group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol, as described below.

In one embodiment, the functionalized copolymer magnetic nanoparticles 100 include an LCST above body temperature and functional groups on their surface for conjugation of biomolecules. NIPA-AAm-AH coated MNPs have a significantly higher percent release at 41° C. compared to that of 4° C., which demonstrates temperature sensitivity and LCST above body temperature (~36.8-37.5° C.). Most preferably, the LCST is above body temperature at least about 37-45° C., preferably between at least about 38-43° C., most preferably between at least about 40-42° C. The functional groups on the surface of the functionalized copolymer magnetic nanoparticles 100 may be conjugated to poly(ethylene glycol) (PEG) and/or targeting biomolecules or molecules to increase the half-life and targeting capability of the functionalized copolymer magnetic nanoparticle. Additional layers of NIPA-AAm-AH decrease the saturation magnetization of the functionalized copolymer magnetic nanoparticles 100.

To synthesize the functionalized copolymer magnetic nanoparticles 100, two synthetic steps may be used. First, MNPs are covalently bound with vinyltrimethoxysilane ("VTMS") to produce a template site for radical polymerization. NIPA, AAm, and AH are then polymerized on the silicon layer around the MNPs via methylene-bis-acrylamide as a crosslinking agent and ammonium persulfate as an initiator. Secondly, the functionalized copolymer magnetic nanoparticles 100 may be formed with silane coated magnetic nanoparticles (MNPs), which are used as a template for a free radial polymerization of three monomers, N-isopropylacrylamide, acrylamide, and allylamine, on the surface of MNPs.

In one embodiment, magnetic nanoparticles may be manufactured by a co-precipitation method. The co-precipitation method may comprise ferric chloride hexahydrate and ferrous chloride tetrahydrate at a ratio of 2:1 dissolved in 600 ml de-ionized (DI) water. After purging the solution with Ar gas, 0.36 g docusate sodium salt (AOT) in 16 ml hexane is added as a surfactant, and the solution was heated to 85° C., at which point 7.1 M NaOH is added. After a 2 hour reaction period, particles are washed extensively with ethanol and then centrifuged at 25000 rpm for 45 minutes. The pellet was dried in a vacuum oven to obtain $Fe_3O_4$ or $Fe_2O_3$ nanoparticles.

Alternatively, other magnetic nanoparticles may be used and prepared accordingly to one of ordinary skill in the art. For example, the magnetic nanoparticles may be prepared by the polyol process, utilizing ferritin, electrochemical synthesis, spray or laser pyrolysis, or thermal decomposition of organometallic compounds in high-boiling organic solvents containing stabilizing surfactants. Alternatively, the magnetic nanoparticles may be prepared by microemulsion technique; metallic cobalt, cobalt/platinum alloys, and gold-coated cobalt/platinum nanoparticles have been synthesized in reverse micelles of cetyltrimethlyammonium bromide, using 1-butanol as the cosurfactant and octane as the oil phase. The magnetic nanoparticles may include any shape and any nanoparticle having responsivity to a magnetic field, including, but not limited to, metal oxides, ferrious oxide, ferric oxide, gadolinium oxide, mixtures thereof, or mixtures of one or more metal oxide. Other alternative magnetic nanoparticles must be selected with break down properties within body and the ability to attach prosthetic/functional groups such as Fe—Co, Fe—Ni, Fe—Pt, and Co—O magnetic nanoparticles.

Figure 12B:
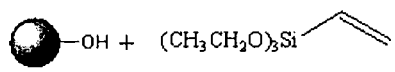
FIG. 12B is a schematic illustration of the preparation procedure of the coated magnetic nanoparticles with VTMS.

In one embodiment, the magnetic nanoparticles are coated with vinyltrimethoxysilane (VTMS) via acid catalyst hydrolysis, followed by electrophilic substitution of ferrous oxide on the surface of the magnetic nanoparticles, as shown in FIG. 12B. Alternative types of VTMS may include additional carbon chains to increase the length of the silane and obtain different properties; and the silane strongly bonds to the magnetic nanoparticle. Alternatively, other functional groups besides an allyl group may be used, i.e. amine, hydroxyl, and the like, to react with the functionalized copolymers. In one example, 0.487 ml VTMS is hydrolyzed using 3 ml acetic acid in the presence of water and ethanol (1:100 v/v). 0.074 g of magnetic nanoparticles are then dispersed by sonication at 100 W for 30 minutes in this solution; the VTMS-coated magnetic nanoparticles was then obtained after 24 hrs of vigorous mechanical stiffing at room temperature. The VTMS-coated magnetic nanoparticles are excessively washed with a mixture of water/ethanol (1:100 v/v) by using an external magnet to collect the products, and the VTMS-coated magnetic nanoparticles are then dispersed in water before polymerizing with copolymer monomers.

VTMS-coated magnetic nanoparticles are used as a template to polymerize copolymer monomers in an aqueous micellar solution, as shown in FIG. 12C. SDS and BIS may be used as surfactant and cross linking agent, respectively. In one example, 0.028 g of VTMS-coated magnetic nanoparticles, 0.1 g of NIPA, 0.0129 g of AAm, 0.0345 ml of AH, 0.0131 g of BIS, and 0.041 g of SDS are sonicated in 100 ml of cold water for 30 minutes. 0.078 g of APS and 101 µL of TEMED are added to the sonicated solution and the reaction was carried out at room temperature under Argon for 4 hours. The amount of NIPA, AAm, and AH used in the starting materials determine the % mole composition for NIPA, AAm, and AH in the final polymerized product. AH does not change the LCST and is only needed enough to just coat the surface with antibody, so the percentage of AH can be changed according to preferences for functionalizing the functionalized copolymer nanoparticles. The functionalized copolymer magnetic nanoparticles may be purified several times with DI water by using a magnet to collect only functionalized copolymer magnetic nanoparticles.

SEM may be used to analyze the average size and morphology of the synthesized functionalized copolymer magnetic nanoparticles. SEM samples may be prepared by coating dried functionalized copolymer magnetic nanoparticles with gold on a silicon wafer. In addition, TEM may be used to determine the size and core-shell structure of the functionalized copolymer magnetic nanoparticles. In general, functionalized copolymer magnetic nanoparticles samples are prepared by drop casting an aqueous dispersion of functionalized copolymer magnetic nanoparticles onto a carbon coated copper grid and the grid was dried at room temperature before viewing under the TEM. Functionalized copolymer magnetic nanoparticles were stained with phosphotungstic acid at a concentration of 0.01% before TEM analysis.

Figure 13:
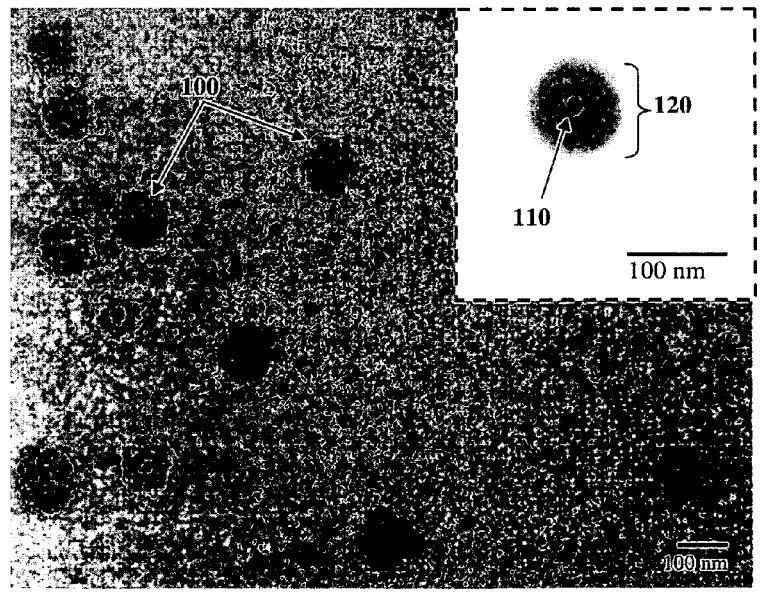
FIG. 13 is a transmission electron micrograph of the functionalized copolymer magnetic nanoparticles, and the inset is a higher magnification image of the functionalized copolymer magnetic nanoparticle.

In one embodiment, the synthesized functionalized copolymer magnetic nanoparticle is approximately 100 nm in diameter, as shown in FIG. 13. A close examination of the TEM image, inset in FIG. 13, shows that the magnetic core 110 (approximately 10 nm) in the center of the functionalized copolymer magnetic nanoparticle with the copolymer shell 130 surrounding the magnetic core 110. The NIPA coated magnetic nanoparticles included less agglomeration of nanoparticles observed under TEM, which is indicative of the electrostatic charge repulsion due to the amine group of allylamine in the copolymer shell. Therefore, encapsulation of magnetic nanoparticles with allylamine provides a functional group on the copolymer shell for bioconjugation and also prevents the agglomeration of the nanoparticles.

Figure 14:
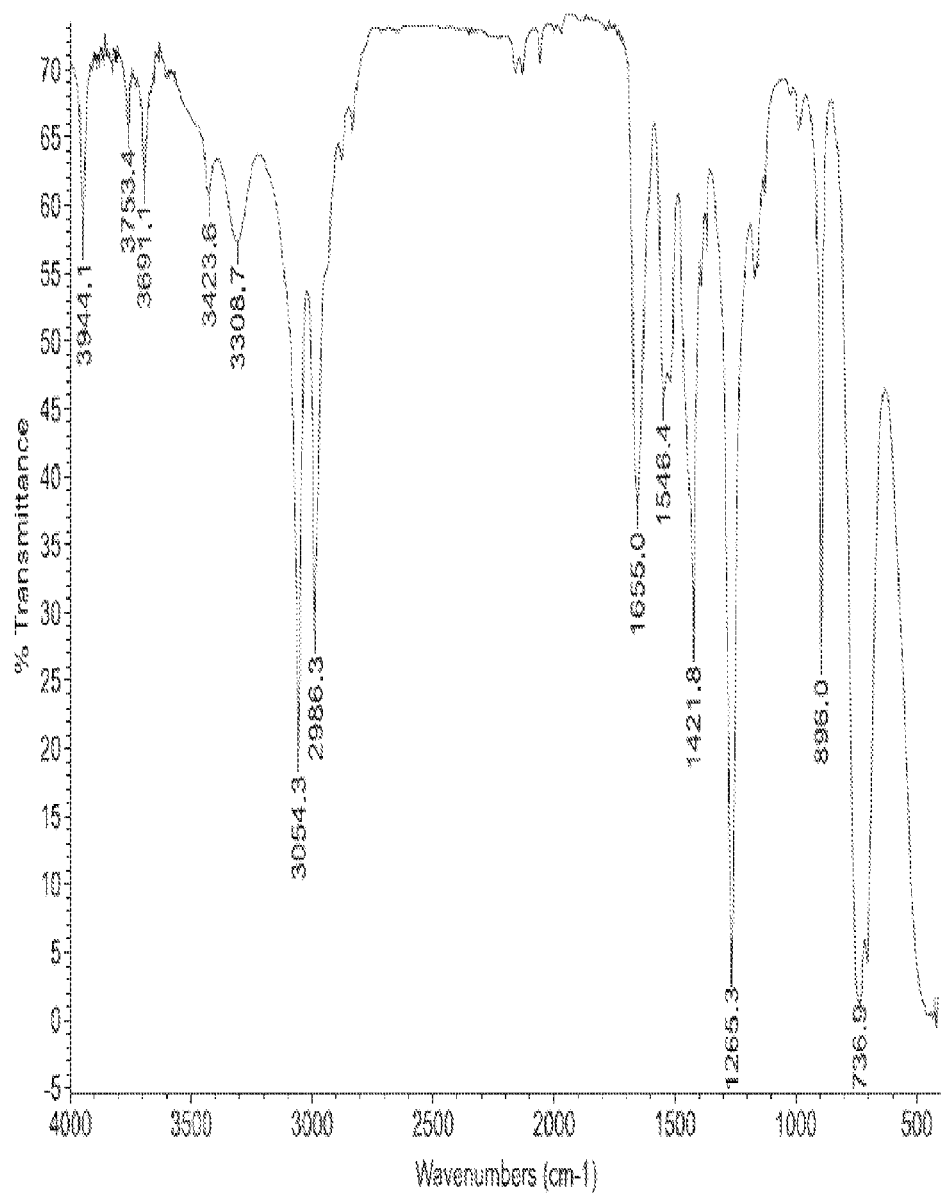
FIG. 14 is a FTIR spectrum of the functionalized copolymer magnetic nanoparticle at room temperature (25° C.) showing the chemical composition analysis of the nanoparticle.

FTIR and X-ray photoelectron spectroscopy (XPS) may be used to characterize the chemical compositions of nanoparticles after each synthesis step. Dried samples were ground with KBr and the mixture was compressed into pellets. FTIR spectra were recorded in the transmission mode using a Bruker VECTOR 22 spectrometer. The spectrum was taken from 4000 to 400 $cm^{-1}$. The FTIR analysis indicated Fe—O of the functionalized copolymer magnetic nanoparticles at 590.3 $cm^{-1}$ and 636.2 $cm^{-1}$, as shown in FIG. 14. As shown in the FIG. 14, the stretching vibration appeared in the range of 2900-3100 $cm^{-1}$ corresponds to C—H bands. The IR peak at 3423 $cm^{-1}$ corresponds to stretching vibration of primary amine group in the functionalized copolymer magnetic nanoparticles. The peak from the secondary amine group is observed around 3308.4 $cm^{-1}$. Furthermore, the carbonyl group from amide functional group of NIPA and AAm is observed at 1655 $cm^{-1}$. These peaks indicate that the functionalized copolymer magnetic nanoparticle is consist of functional groups corresponding to it's constitute monomers, as shown in FIG. 14.

XPS measurements may be carried out on the synthesized functionalized copolymer magnetic nanoparticles on a Perkin-Elmer PHI560 ESCA/SAM system using an Al Kα 1486.6 eV X-ray source. The resolution of the analyzer was 0.5 eV. Deconvolution may be carried out with Gaussian functions. Chemical states of various elements may be obtained by using binding energies from the known literature sources. The atomic percentage of the elements present in the particles was calculated from the ratio of the net intensities of corresponding peaks, corrected using the instrument's sensitivity factors.

Figure 15A:
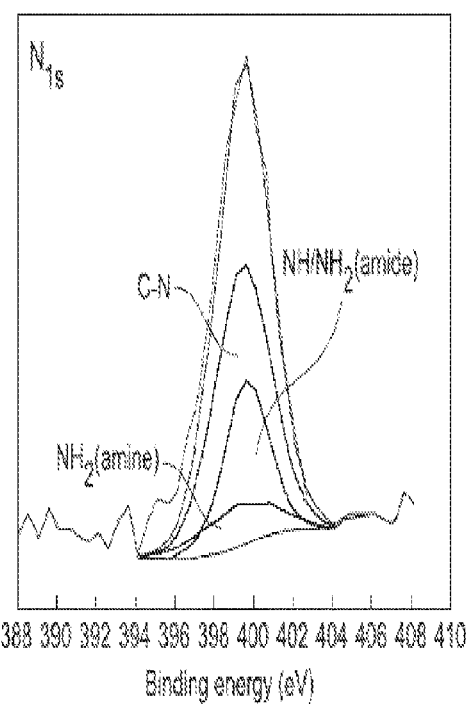
FIG. 15A-E are graphs of the high resolution deconvoluted spectra from 15A) N 1s, 15B) Si 2p, 15C) Fe $2_{1/2}$, 15D) O 1s, and 15E) C 1s of the NIPA-AAm-AH coated MNPs (i.e. functionalized copolymer nanoparticles), respectively.

High resolution scans of the functionalized copolymer magnetic nanoparticles were performed for the various elements involved in order to obtain detailed information on the chemical bonds. FIG. 15A shows the N 1s spectrum of the functionalized copolymer magnetic nanoparticles. The result indicates the presence of different amine functional groups in the functionalized copolymer magnetic nanoparticles. The peak at 399.6 eV was deconvoluted with a Gaussian peak for amine, C—N, and amide bond at 399.33, 399.52, and 399.7 eV, respectively, which is close to the binding energy reported earlier. The XPS results in FIG. 15A indicate that N 1s are mostly present as C—N. Table 2 provides the various % ages of the three chemical states.

Figure 15B:
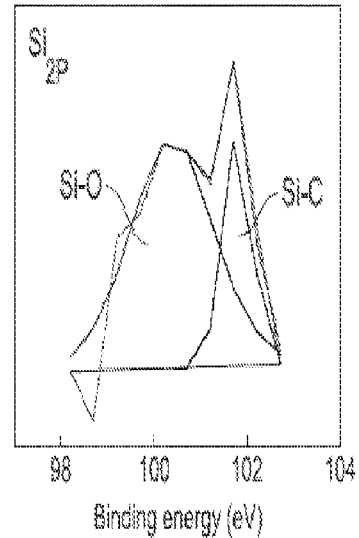

The Si 2p high resolution spectrum obtained from the functionalized copolymer magnetic nanoparticles is shown in FIG. 15B. The Si 2p peak clearly shows two peaks, and it is composed of a Si—O bond (100.4 eV) and a Si—C bond (101.8 eV), which indicates the existence of both Si—C and Si—O bonds in the functionalized copolymer magnetic nanoparticles. The percentages of Si—O and Si—C are 74.8% and 25.2% (ratio of 3:1), indicating that each Si atom in the particles is bonded with three O atoms and one C atom.

Figure 15C:
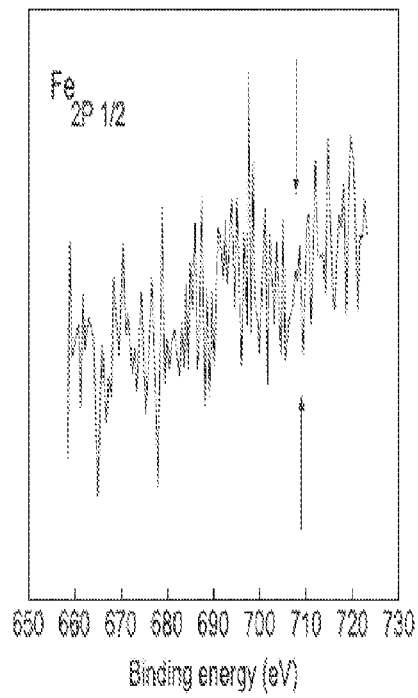
Figure 15D:
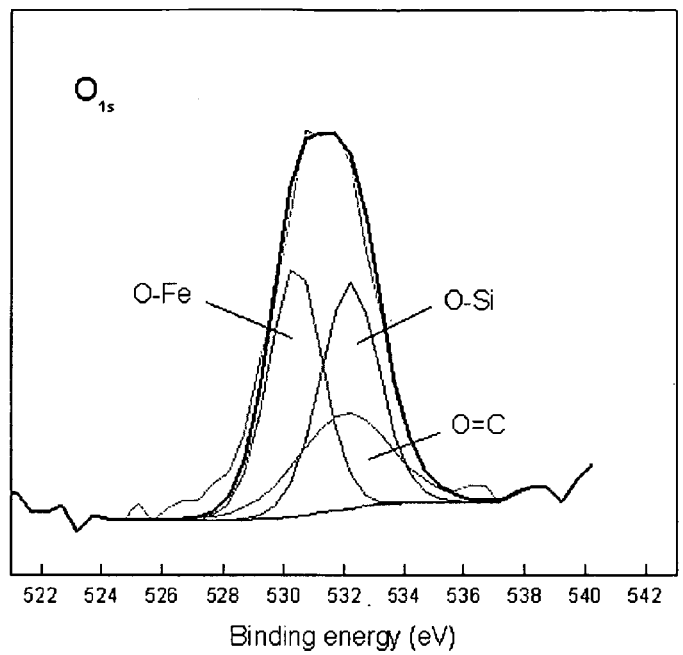

Due to the existence of Fe—O, C═O, and Si—O bonding, the O 1s spectrum should be fitted with three peaks corresponding to 530.37, 532, and 532.18 eV, as shown in FIG. 15D. In comparison to the O 1s spectrum of an empty shell of copolymer shell 120, the spectrum of copolymer core-shell magnetic nanoparticles has shifted from 531.95 to 531.32 eV, respectively. The 531.95 to 531.32 eV shift is due to the presence of Fe—O and Si—O in the copolymer shell 120.

Figure 15E:
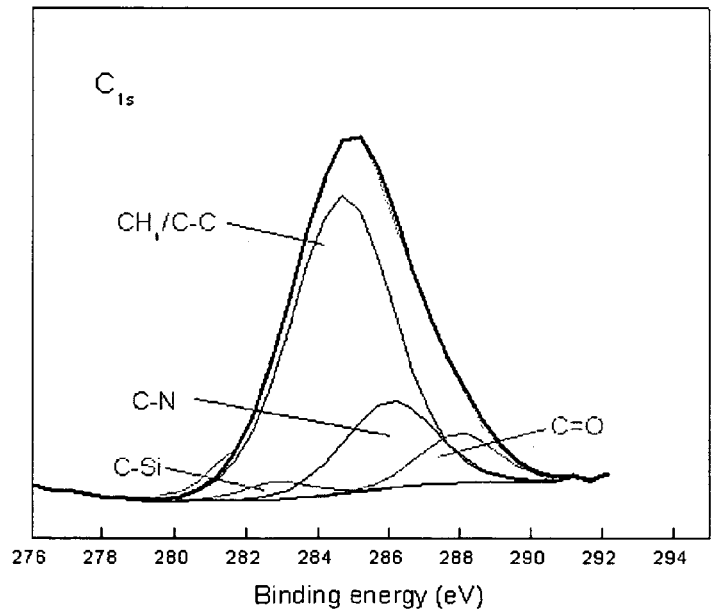

The C 1s high resolution spectrum obtained from the functionalized copolymer magnetic nanoparticles consists of a binding energy of 285.01 eV as shown in FIG. 15E. The C 1s spectrum was fitted with four peaks at 284.7, 282.9, 286.04, 287.98 eV, corresponding to $CH_n$/C—C, C—Si, C—N, and C═O bonds, respectively, as shown in FIG. 15E. The relative content for the different C bonding states was calculated to be 69.93%, 2.76%, 18.5%, and 8.81%, respectively. The high content of the $CH_n$/C—C bond indicates that the majority of the C in the spectra originates from the polymer shell. Table 2 illustrates the detail bonding energy, peak area, and percent composition for each group. In contrast to other elements, the binding energy of Fe 2p½ was not observed in FIG. 15C, which might be due to the thick coating of the copolymer shell 120. The absence of the Fe peak in coated MNPs ensures a complete coating in the copolymer shell.

TABLE 2

The peak area in XPS spectra of functionalized copolymer magnetic nanoparticles

| Element | Chemical State | Binding Energy (eV) | Peak Area | % Composition |
|---|---|---|---|---|
| $C_{1s}$ | C—C/CHn | 284.7 | 22727.9 | 69.9 |
|  | C—Si | 282.9 | 896.5 | 2.8 |
|  | C—N | 286.04 | 6014.4 | 18.5 |
|  | C═O | 287.98 | 2863.8 | 8.8 |
| $O_{1s}$ | O—Fe | 530.37 | 5900.4 | 37.4 |
|  | O═C | 532 | 3997.8 | 25.3 |
|  | O—Si | 532.18 | 5893.1 | 37.3 |
| $N_{1s}$ | $NH_2$ (amine) | 399.33 | 1019 | 11.9 |
|  | C—N | 399.52 | 5126.7 | 60 |
|  | $NH/NH_2$ (amide) | 399.7 | 2398 | 28.1 |
| $Si_{2p}$ | Si—C | 101.8 | 49.1 | 25.2 |
|  | Si—O | 100.2 | 145.8 | 74.8 |

A magnetic property measurement system with a Superconducting Quantum Interference Devices (SQUID)-based magnetometer (Quantum Design) may be used to obtain room temperature magnetic hysteresis loops for MNPs, silane-coated MNPs, and copolymer coated MNPs. Pre-weighed samples are placed in a gelatin capsule, and the capsule with the pre-weighed sample is mounted in a transparent drinking straw wherein the measurement may be obtained.

Figure 16:
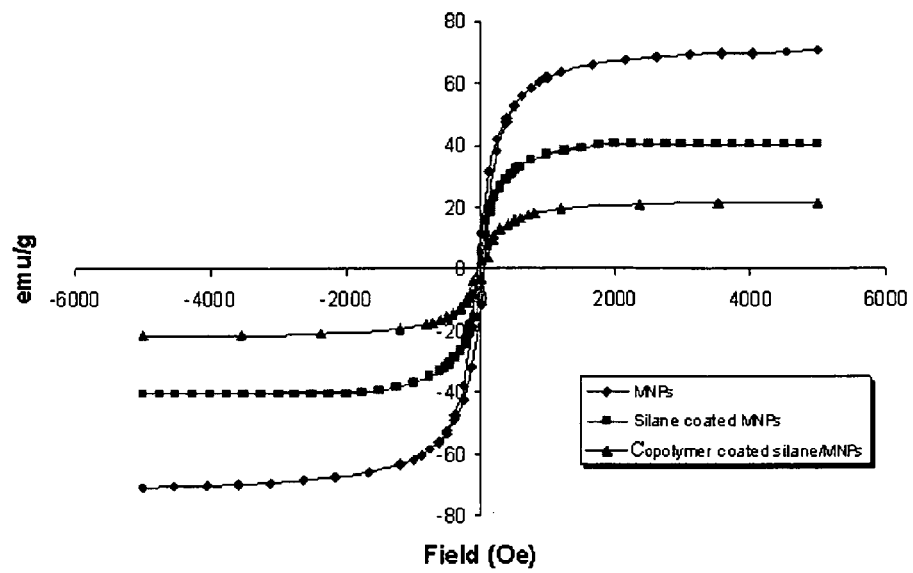
FIG. 16 is a graph of the magnetic hysteresis curve of magnetic nanoparticles, silane coated, and functionalized copolymer magnetic nanoparticles at room temperature.

Room temperature magnetization measurements of magnetic nanoparticles, silane coated magnetic nanoparticles and functionalized copolymer magnetic nanoparticles were determined using a SQUID-based magnetic property measurement system, as shown in FIG. 16. The saturation magnetization of the MNPs is 70.86 emu/g, which is lower than bulk iron oxide (87.25 emu/g), and this behavior is a non-linear spin configuration on the surface, resulting from the incomplete or different surroundings of the surface atoms. The magnetic nanoparticles and the two layers is classified as soft ferromagnetic substance due to their low coercive force (<$10^2$ Oe), small remanent magnetic induction, and long and narrow hysteresis loop. The values of magnetic properties of each nanoparticle are shown in Table 3.

TABLE 3

Magnetic properties of the MNPs.

| Sample | Saturation Magnetization ($M_s$) emu/g | Remanence ($M_r/M_s$) | Coercivity ($H_c$) Oe |
|---|---|---|---|
| MNPs | 70.861 | 11.42 | 9.53 |
| Silane coated MNPs | 40.217 | 5.53 | 26.69 |
| Copolymer coated MNPs | 21.552 | 3.10 | 37.80 |

The saturation magnetization of functionalized copolymer magnetic nanoparticles was decreased by 43.2% after coating with silane and by 69.6% after coating with the copolymer shell. The decrease in saturation magnetizations are due to "dead" surface layer on magnetic nanoparticles present on the surface of functionalized copolymer magnetic nanoparticles. This decrease was also observed when the functionalized copolymer magnetic nanoparticles were placed in an external magnetic field where increase in their response time was noticeable. Furthermore, the coercivity increased as the MNPs were coated with silane and copolymer, which is due to size effects and an increase in separation distance of nanoparticles as a result of coating.

In order to increase the circulation half life of functionalized copolymer magnetic nanoparticles, green fluorescent poly ethylene glycol (PEG) with carboxylic activated group may be used. PEG with MW of around 3000 Da is preferable. PEG incorporation onto the surface of nanoparticles would induce the circulation half life of the particles. The amine groups on the magnetic nanoparticles would be easier to incorporate thus PEG with carbosylic ends, whereby there is covalently binding between carboxylic and amine groups. AH contain amine group and PEG is functionalized with carboxylic acid group therefore the two can be reacted to form amide bond. Alternative functionalization steps are provided in the Examples section. In one example, 0.01 g of NIPA-AAm-AH coated MNPs is dispersed in 0.5 ml of MES (0.1 M) buffer solution and 0.01 g of EDC is added. The reaction is mixed well for 10 minutes at room temperature and 0.2 mg of Fluor-PEG-SCM (FPS) is added to the above solution and the reaction is stirred vigorously for 24 hours at room temperature under dark conditions. The product is purified several times with DI water by using an external magnet to remove un-reacted FPS. The sample is lyophilized and resuspended in 50% glycerol in water before imaging.

Figure 17:
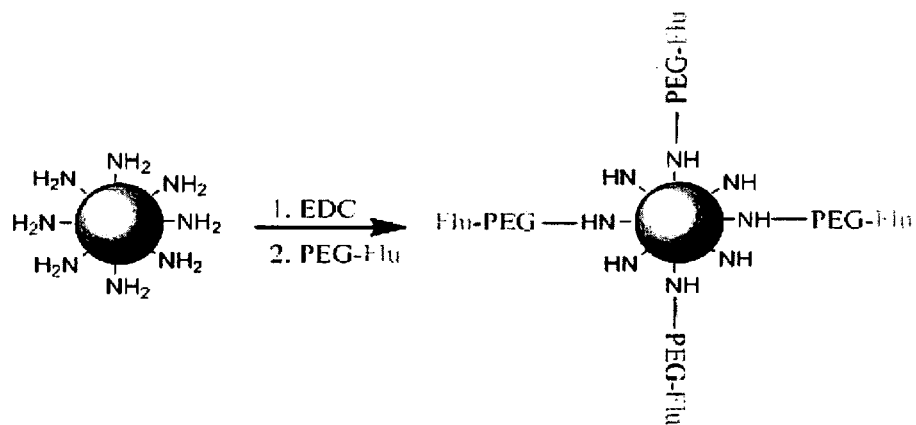
FIG. 17 is a schematic diagram of the conjugation reaction of NIPA-AAm-AH coated MNPs with fluorescent PEG.
Figure 18A:
FIGS. 18A-B are images of NIPA-AAm coated MNPs reacted with fluorescent PEG using phase contrast enhanced optical microscopy and fluorescent enhanced optical microscopy, respectively.
Figure 18B:
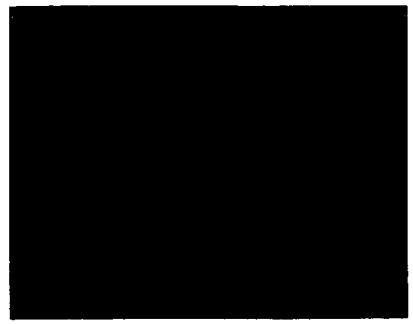
Figure 18C:
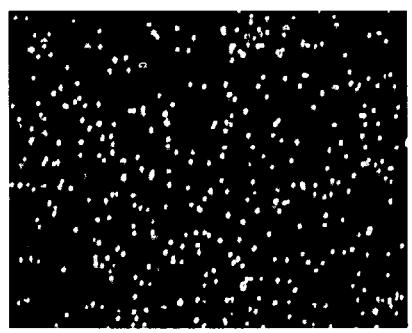
FIGS. 18C-D are images of the functionalized copolymer nanoparticles reacted with fluorescent PEG using phase contrast enhanced optical microscopy and fluorescent enhanced optical microscopy, respectively.
Figure 18D:
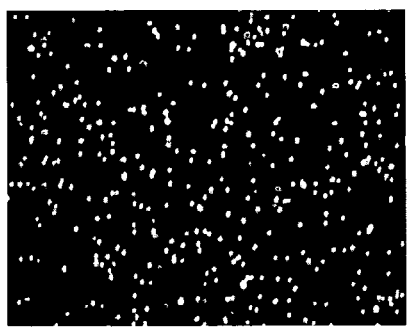

Fluorescent PEG may be conjugated to the functionalized copolymer magnetic nanoparticles by using the carbodiimide chemistry, as shown in FIG. 17. Enhanced optical fluorescence microscopy was used to assess the attachment of fluorescent PEG to the functionalized copolymer magnetic nanoparticles (NIPA-AAm-AH coated MNPs). FIGS. 18A-D indicates a bright green color was observed on NIPA-AAm-AH coated MNPs, whereas this fluorescence was not seen in NIPA-AAm coated MNPs.

For drug loading and release studies, bovine serum albumin (BSA) may be used as a model protein. Alternatively, any pharmacologically active or therapeutic agent may be loaded into the functionalized copolymer magnetic nanoparticles selected from the group of antibiotic drugs, antiviral drugs, anti-cancer drugs, chemotherapy drugs, steroids, anti-clotting drugs, aspirin, antiproliferative agents, antioxidants, antimetabolites, non-steroidal and steroidal anti-inflammatory drugs, immunosuppressants, genetic materials including DNA & RNA fragments.

In one embodiment to load the functionalized copolymer magnetic nanoparticles, 0.06 g of lyophilized functionalized copolymer magnetic nanoparticles and 0.005 g/ml of BSA is dispersed in 20 ml of de-ionized water. The solution is stirred at 4° C. for 3 days. The BSA encapsulated functionalized copolymer magnetic nanoparticle is separated from solution via an external magnet. The solution is then analyzed using a BCA protein assay kit (PIERCE) following the manufacturer's instructions to determine the amount of BSA in the dialysate. This value is then compared with the total amount of BSA (Protein) used in the nanoparticle formulation protocol to determine the BSA loading efficiency of the particles. Loading efficiency was calculated according to the Equation (2):

$$\% \text{ Loading Efficiency} = \frac{\text{total [Protein] used in nanoparticle formulation} - \text{[Protein] present in solution}}{\text{total [Protein] used}} \times 100\% \quad (2)$$

The drug release profile of the synthesized functionalized copolymer magnetic nanoparticles may be investigated with 2 ml of drug loaded nanoparticle solution may be placed inside dialysis bags with a MWCO of 100,000. Samples are then dialyzed against de-ionized water at 4° C. and 41° C. At designated time intervals, 1 ml of dialysate is removed from each sample and stored at −20° C. for later analysis. Dialysate volume is reconstituted by adding 1 ml of fresh de-ionized water to each sample. Dialysate samples are analyzed using the BCA protein assay kit to determine the amount of BSA released into the dialysate following the manufacture's instructions.

Figure 19A:
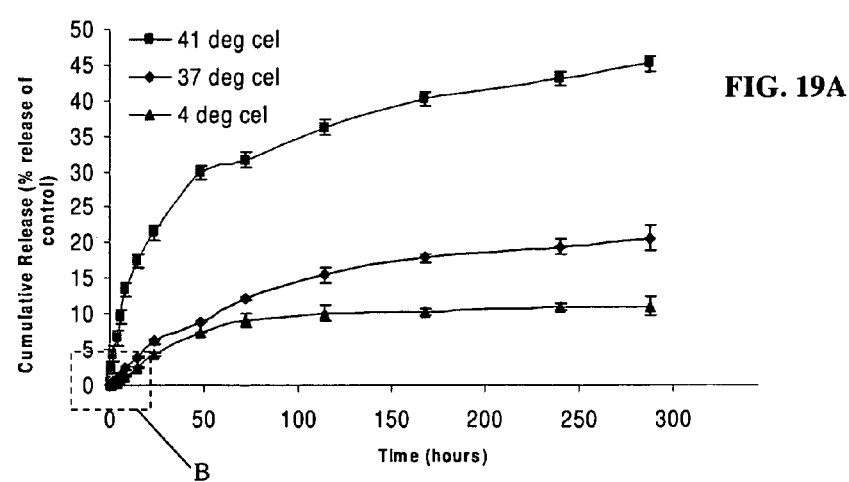
FIG. 19A is a graph of the in vitro release profile of BSA at 4° C., 37° C., and 41° C. and the cumulative percent release of BSA over 300 hours.
Figure 19B:
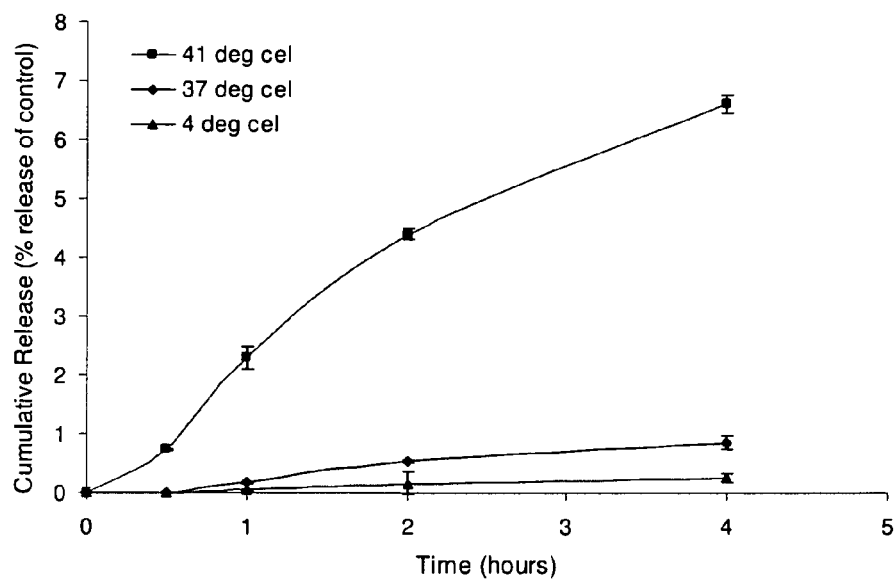
FIG. 19B is the cumulative percent release of BSA over 4 hours, an exploded view of section B in FIG. 19A.

The loading efficiency of BSA encapsulated functionalized copolymer magnetic nanoparticles was determined according to Equation (2). The protein assay indicated that approximately 73% of the incubated BSA was loaded into the functionalized copolymer magnetic nanoparticles. The release behavior of the nanoparticles was studied for approximately 300 hours in PBS (0.1 M, pH 7.4) at 4° C. and 41° C. Percent cumulative release of BSA at 41° C. was significantly higher than at 4° C., as shown in FIGS. 19A-B, which indicates that the copolymer nanoparticle is temperature sensitive polymer whereby at its LCST the nanoparticles collapse upon itself and squeeze the drug out. After 300 hours, 45% of the encapsulated BSA was released at 41° C. whereas at 4° C. approximately 11% is released. In addition, the low BSA release may be due to BSA interacts with polymer and itself where it hinders its release. The release profile of the BSA over first 4 hours is also shown in FIG. 19B. After 4 hours, the cumulative percent release of BSA is only 0.3% at 4° C. whereas at 41° C. is 6%. The observed burst release of drug at this short period of time is useful for applications such as cancer treatment where aggressive measures need to be taken to treat the disease.

Figure 20A:
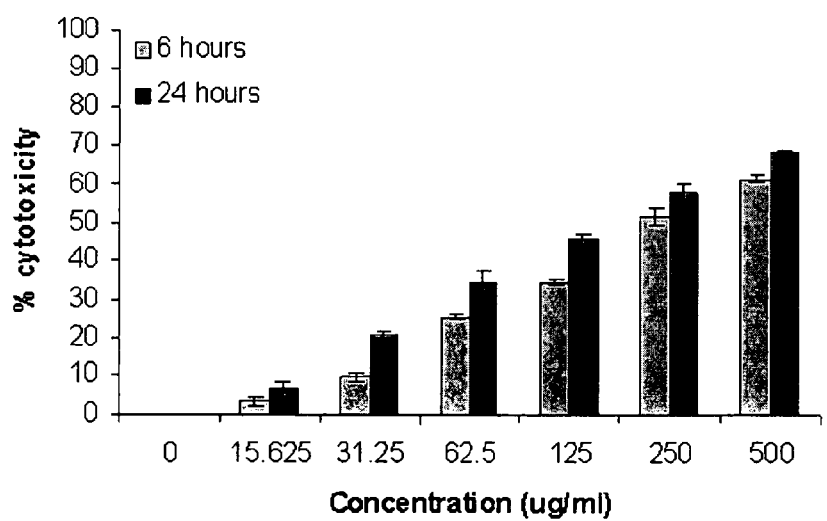
FIG. 20A is a graph of the cytotoxicity of magnetic nanoparticles.

In order to assess the biocompatibility of copolymer-MNPs, their cytotoxicity may be tested. Nanoparticles are incubated in wells with 3T3 fibroblasts for 24 hours at various concentrations (0, 15.6, 31.2, 62.5, 125, 250 and 500 µg/mL). Two types of nanoparticles are used; the original magnetic nanoparticles and the copolymeric coated magnetic nanoparticles. Cell death in the media is analyzed using a Lactate Dehydrogenase (LDH) Assay (Promega Corporation, Wisconsin) and read on a microplate reader at 490 nm. The biocompatibility of the magnetic nanoparticles and manufactured nanoparticles is determined by qualifying the cell death of 3T3 fibroblasts by the reader. The LDH index of cytotoxicity released in the media from cultured fibroblasts may be analyzed in order to assess the plasma cell membrane damage caused by exposure to either original MNPs or copolymer MNP's (NIPA-AAm-AH coated MNPs as shown in FIG. 21C. Cells exposed to 1% Triton solution serve as positive controls (100% cell death or cytotoxicity). Results from LDH Assays after 6 hours showed that the presence of magnetic nanoparticles at the concentration range of 15.6 to 31.2 µg/ml reduce the normal cells' viability by less than 20%, as shown in FIGS. 20A-B. Higher concentrations after 6 hours showed significant cytotoxicity to as high as 62% for 500 µg/ml. Presence of magnetic nanoparticle after 24 hours at concentration of 31.2 µg/ml and higher showed significantly higher cytotoxicity (>20%) compared to 6 hours incubation. The cytotoxicity of magnetic nanoparticles after 24 hours was 68% at 500 µg/mL. Unlike magnetic nanoparticles, the functionalized copolymer magnetic nanoparticles are much less cytotoxic, as shown in FIGS. 20A-C. The highest cytotoxicity was observed at 500 µg/mL of functionalized copolymer magnetic nanoparticles after 24 hours which was approximately only 20%, which illustrates that magnetic coated copolymer nanoparticles are much more compatible compare to magnetic nanoparticles, especially when nanoparticles are used at high concentrations. These results demonstrate that the functionalized copolymer magnetic nanoparticles are more biocompatible at high concentrations compared to the original iron oxide magnetic nanoparticles as shown in FIG. 21C Comparing the cellular uptake of NIPA and functionalized copolymer magnetic nanoparticles may give a better understanding of in vitro behavior.

In order to characterize in vitro behavior, cell uptake studies were performed. Prostate cancer cells (JHU31), American Type Culture Collection (ATCC)), were cultured to confluence, harvested after trypsinization and dispersed in complete DMEM (Invitrogen) supplemented with 10% fetal bovine serum (Hyclone) and 1% penicillin-streptomycin. Cells were seeded at density of approximately 10,000 cells/well in 24-well plates. The cells were incubated for 24 hours at 37° C. To investigate the effects of nanoparticle optimal dosage and incubation time, functionalized copolymer magnetic nanoparticles were added at various concentrations (0, 125, 250, 300, 500, 800 and 1000 µg/mL) in the cell sample and incubated for 6 and 24 hours. After incubation, cells were lysed with 1% Triton in PBS. Similarly, to test for the optimal incubation time, 500 µg/mL of functionalized copolymer magnetic nanoparticles were added to a 24-well plate and incubated for varying durations (0, 0.5, 1, 2, 4, 6 and 8 hours). After predetermined times, the cells were lysed with 1% Triton in PBS.

To determine the amount of Fe uptake, an Iron Content Assay may be performed. In one example, cell lysate was incubated in HCL at 50° C. for 2 hours and then ammonium persulfate was added. After shaking for 15 minutes, thiocyanate was added and the samples were shaken for another 15 minutes before being read on a microplate reader at 540 nm. The cell lysate was tested for DNA content using a Picogreen Assay (Invitrogen Corporation, California) and this data was used to normalize the iron content.

Figure 21A:
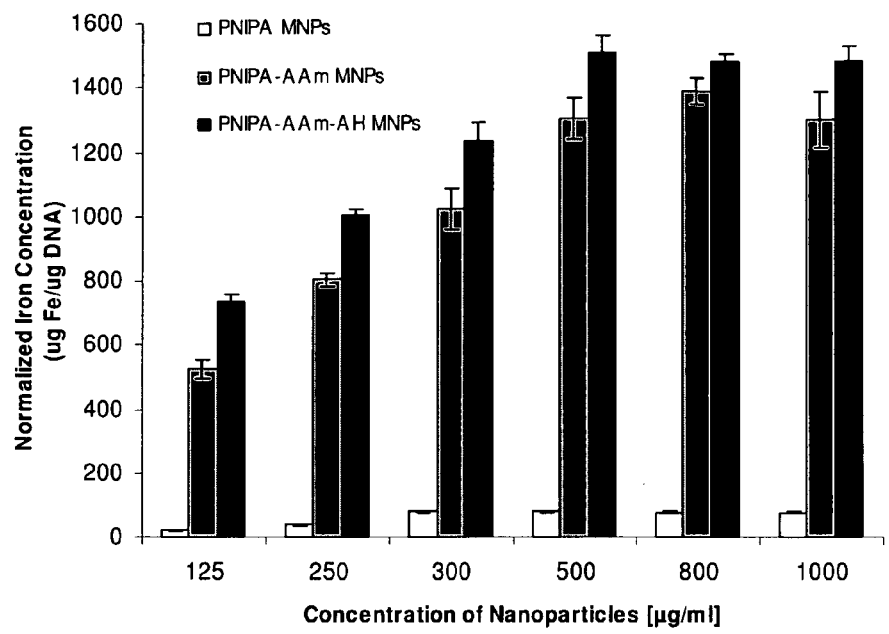
FIG. 21A is a graph of the cellular uptake studies of the effect of concentration on cellular uptake for the MNPs, acrylamide magnetic nanoparticles (PNIPA AAm MNPs), and functionalized copolymer magnetic nanoparticles (PNIPA-AAm-AH MNPs)
Figure 21B:
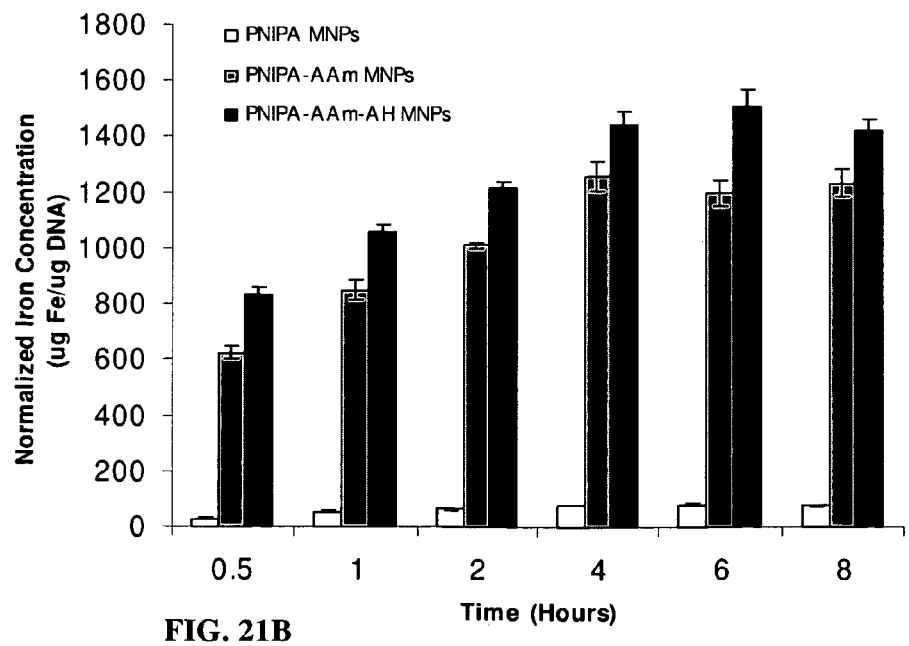
FIG. 21B is a graph of the effect of time on cellular uptake.

In order to determine the optimal concentration of nanoparticles and the optimal incubation time required for the cells to take up NIPA, NIPA-AAm, and functionalized copolymer magnetic nanoparticles by the prostate cancer cell line JHU31 (ATCC). As shown in FIGS. 21A-B, JHU31 cells took up polymeric coated magnetic nanoparticles in a time and concentration-dependent manner. The highest concentration of uptake is when the cells are treated with functionalized copolymer magnetic nanoparticles. Furthermore, the lowest concentration of uptake observed when the cells were treated with NIPA coated magnetic nanoparticles, which might be due to the fact that the LCST of NIPA coated magnetic nanoparticles is below incubator temperature; therefore most of the nanoparticles are aggregated due to hydrophobic attraction and exist as particles larger than nanometer size. Whereas, NIPA-AAm and functionalized copolymer magnetic nanoparticles has LCST above incubator temperature and stay as water soluble and nanoparticles. In order to test this hypothesis, NIPA, NIPA-AAm and functionalized copolymer magnetic nanoparticles were incubated for 30 at 37° C. before measuring their size utilizing a laser scattering particle sizer (Nanotrac). At 25° C. all of the nanoparticles were approximately 100 nm, and at 37° C. the size of NIPA coated magnetic nanoparticles increased to approximately 800 nm, which indicates that the cellular uptake of NIPA coated magnetic nanoparticles was hindered due to hydrophobic attraction and increase in size. NIPA-AAm and functionalized copolymer magnetic nanoparticles maintained in nanometer size. Therefore, this phenomenon might explain the increase in the cellular uptake of functionalized copolymer magnetic nanoparticles in comparison to NIPA coated magnetic nanoparticles. In each of the polymeric coated magnetic nanoparticles, a plateau was formed. The NIPA coated magnetic nanoparticles formed plateau at 300 µg/ml, and NIPA-AAm and functionalized copolymer magnetic nanoparticles formed plateau at 500 µg/ml. The ideal incubation time for the cancer cells to take up particles was shown to be four hours as seen in FIGS. 21A-B.

To investigate the retention of functionalized copolymer magnetic nanoparticles in absence and presence of the magnetic field under physiological conditions, the parallel flow chamber was used as previously described. The cells were seeded onto pre-etched glass slides at a density of $10^5$ cells/$cm^2$. Cells were allowed to attach overnight, and grown for two days before being used in experiments. Before conducting the experiments magnetic copolymers (0.265 mg/ml) were dispersed into culture media via ultra-sonicator. Three different types of shear stress (1, 13, and 21 dyn/cm2) were used by adjusting the flow rates in the flow systems. These different flow rates were applied without a magnetic field and with magnetic field in presence and absence of different cell types (endothelial cells, smooth muscle cells and prostate cancer cells). The percentage retention of magnetic copolymer was determined via measuring concentration of iron from input and output of the flow system.

Figure 22A:
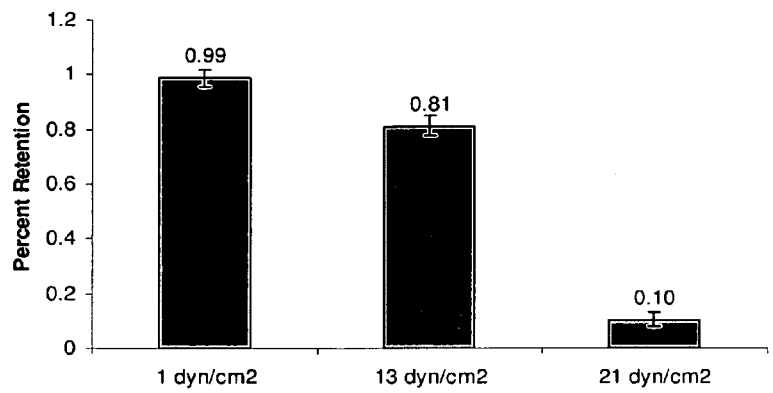
FIGS. 22A-E are graphs of the flow of the magnetic copolymer at different shear stresses.
Figure 22B:
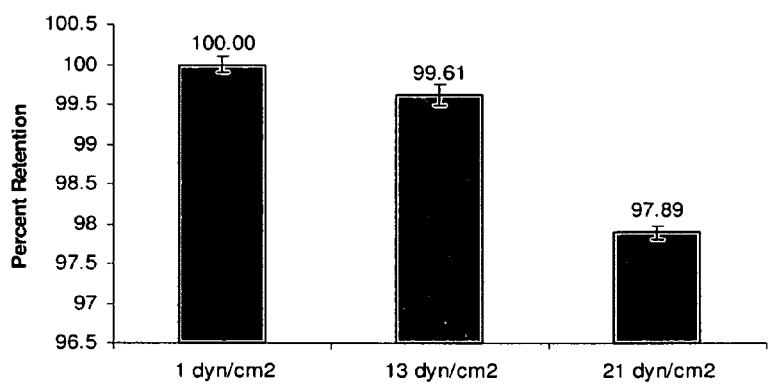
Figure 22C:
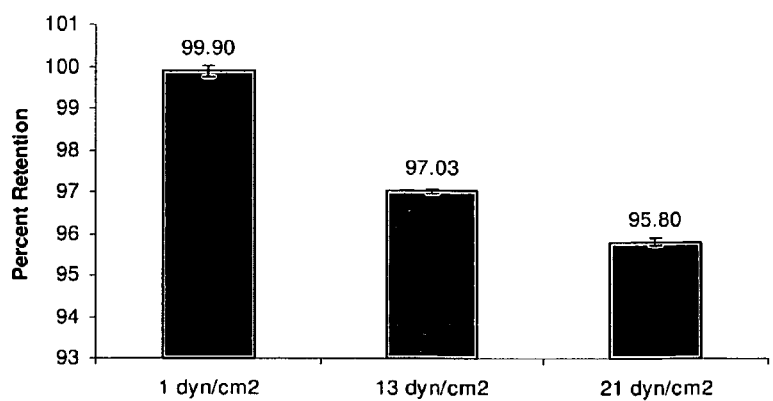
Figure 22D:
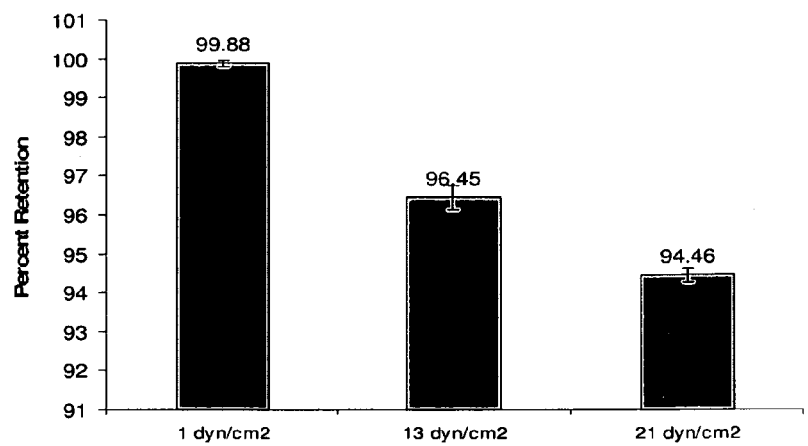
Figure 22E:
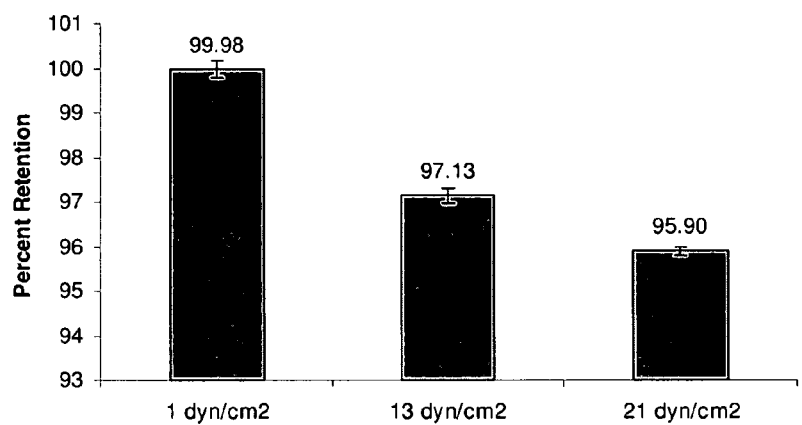

As shown in FIG. 22A, less than 1% retention was observed when no external magnetic field was used. Furthermore, the lowest percent retention was observed when high shear stress (21 dyn/cm$^2$) was used. The retention of the nanoparticles in the absence of external magnetic field is due to the fact that the nanoparticles are positively charged, and it is highly possible that they were entrapped in the system due to the electrostatic attraction. The result is dramatically different in presence of magnetic filed. As shown in FIG. 22B, the lowest percent retention was only 97.89%. This difference between FIG. 22A-B proves how effective the system is as targeted drug delivery system whereby the nanoparticles can be localized in body at disease site using external magnetic field. Furthermore, in each group the lowest percent retention was observed at highest shear stress (21 dyn/cm$^2$) which is the same behavior that was observed without magnetic field. This low retention is due to the fact that the nanoparticles have high velocity at highest flow rate; consequently, the attraction of nanoparticles to the external magnetic field becomes minimal at high flow rate (shear stress).

Figure 23A:
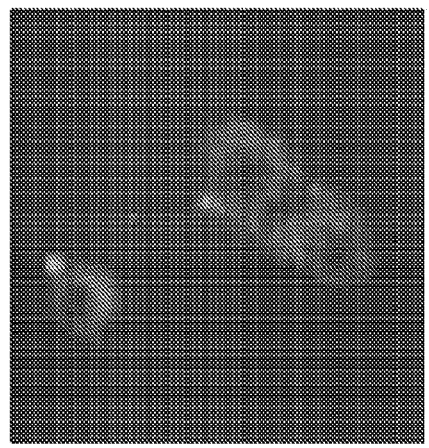
FIGS. 23A-C are confocal images of the uptake of nanoparticles by JHU31 cells using confocal microscopy, where
Figure 23B:
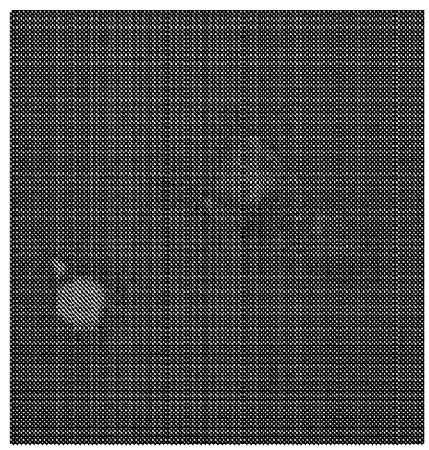
Figure 23C:
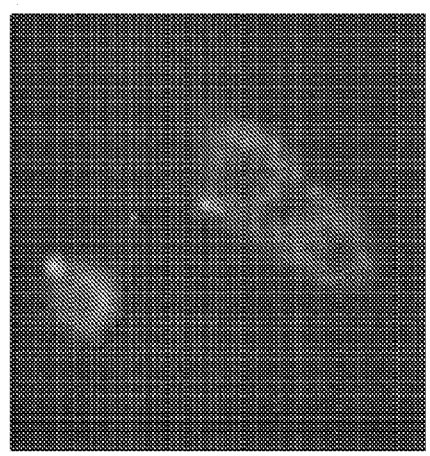

In order to visualize the uptake of PNIPA-AAm-AH coated MNPs, Texas Red (bovine anti-rabbit IgG-Texas Red) was conjugated to the functionalized copolymer magnetic nanoparticles via carbodiimide chemistry. In brief, 0.01 g of PNIPA-AAm-AH coated MNPs was dissolved in 0.5 ml of MES (0.1 M) buffer solution and 0.01 g of NHS and EDC was added. The reaction was mixed well for 10 minutes at room temperature and 0.2 mg of Texas Red was added to the above solution and the reaction was stirred vigorously for 2 hours at room temperature under dark conditions. In order to remove un-reacted Texas Red, the product was purified several times with DI water using an external magnet. The results indicated that nanoparticles are internalized by prostate cancer cells and were accumulated in the cytoplasm, as shown in FIGS. 23A-C. The success of Texas Red antibody conjugation also suggests that the functionalized copolymer magnetic nanoparticles have the functional amine groups for conjugation of biomolecules.

In order to investigate the pharmacological activity of the in vitro released DOX from the functionalized copolymer magnetic nanoparticles, cancer cell viability was conducted using MTS assays (Promega) according to the manufacturer's instruction. Prostate cancer cells (i.e., JHU31) were cultured to confluence, harvested by trypsinization, and dispersed in RPMI supplemented with 10% serum and 1% penicillin-streptomycin. Cells were seeded at a density of approximately 10,000 cells/well in 24-well plates for 24 hours at 37° C., and then were then incubated with nanoparticles, DOX-loaded nanoparticles, and free DOX. The concentration of functionalized copolymer magnetic nanoparticles and DOX-loaded functionalized copolymer magnetic nanoparticles was 500 µg/ml. This nanoparticle concentration was selected according to drug release results from the nanoparticles indicated above and the optimal inhibition dose of DOX on prostate cancer cell growth studies. The prostate cancer cells were incubated with each group at 37° C., 41° C., and temperature cycles between 37° C. and 41° C. (one hour at each temperature for one cycle) for 24 hours.

Figure 24A:
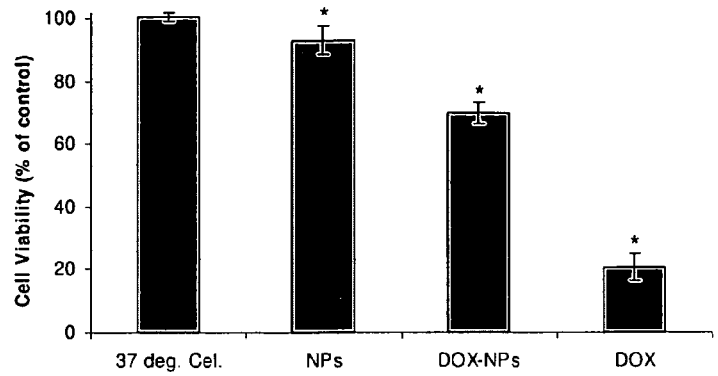
FIGS. 24A-C are graphs of pharmacological activity of DOX loaded PNIPA-AAm-AH coated magnetic nanoparticles (DOX-NPs) in comparison with empty nanoparticles (NPs) and free DOX (DOX)m, where the cell viability was investigated using MTS assays at 37° C., FIG. 24A, 41° C. for FIG. 24B, and temperature cycles between 37° C. and 41° C. (temp. cycle) for FIG. 24C.
Figure 24B:
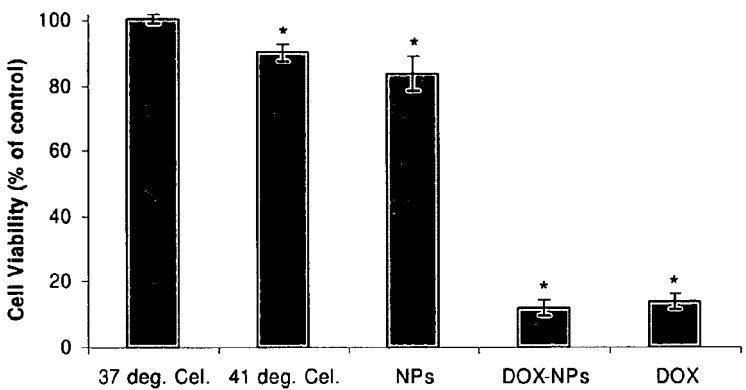
Figure 24C:
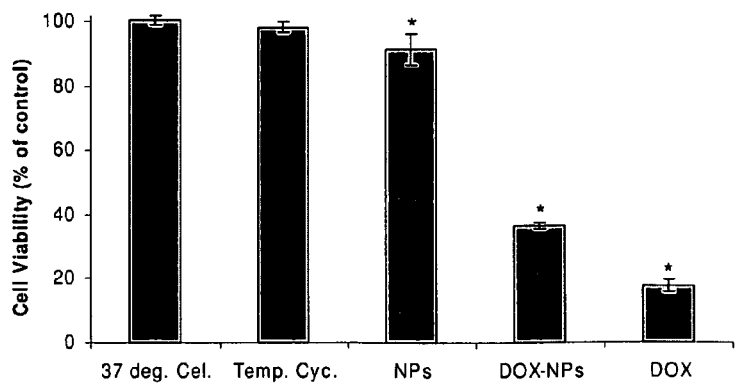

As shown in FIG. 24A, the free DOX decreased cell viability to 20% in comparison to the control. Moreover, DOX-loaded functionalized copolymer magnetic nanoparticles (DOX-NPs) decreased cell viability to 70% at 37° C. When cells were exposed at 41° C. or temperature cycles between 37° C. and 41° C. (one hour each at each temperature for 24 hours), DOX-loaded functionalized copolymer magnetic nanoparticles could decrease the cell viability to 12% or 36%, respectively, as shown in FIGS. 24B and 24C). The decreases in cell viability are much more significant, especially at 41° C., in comparison to 37° C., which is an indication that the copolymer magnetic nanoparticle drug delivery system is temperature sensitive and the released drugs are pharmacologically active. DOX-loaded polymer-coated MNPs (e.g. PEG coated MNPs) release pharmacologically active DOX with a high activity of cell killing.

In the presence of a magnetic field, different cell types had slightly different percent retention. Endothelial cells, smooth muscle cells, and prostate cancer cells were chosen to show the percent retention of functionalized copolymer magnetic nanoparticles. In the presence of external magnetic field there is more than 93% increase in retention of nanoparticles which is highly significant as a localized drug delivery system.

The release profile of therapeutic drugs from nanoparticles at various temperatures and pHs, as indicated previously, as well as targeted capability of the synthesized nanoparticles for possible applications in controlled and targeted delivery may be investigated.

Example 1

Shear-Regulated Uptake of Nanoparticles by Endothelial Cells

The polymer nanoparticles may include targeting, adhesion, and cellular uptake to activated or inflamed endothelial cells (ECs) under physiological flow conditions. Under diseased conditions such as thrombosis, inflammation, and restenosis, ECs become activated and express endothelial cell adhesion molecules (ECAMs) such as P-selectin and E-selectin. The polymer nanoparticles mimic the binding of platelets with activated ECs such as the binding of platelet glycoprotein Ibα (GP Ibα) with P-selectin expressed on activated endothelial cells, GP Ibα-conjugated temperature sensitive nanoparticles exhibit increased targeting and higher cellular uptake in injured or activated endothelial cells under physiological flow conditions.

Fluorescent carboxylated polystyrene nanoparticles were selected as a model particle. Conjugation of 100 nm polystyrene nanoparticles with glycocalicin (the extracellular segment of platelet GP Ibα) significantly increased the particle adhesion on P-selectin-coated surfaces and cellular uptake of nanoparticles by activated endothelial cells under physiological flow conditions. It should be appreciated that the functionalized copolymer nanoparticles and the functionalized copolymer magnetic nanoparticles may be conjugated to glycocalicin in a similar fashion, whereby the functionalized amine group is covalently bound to a carboxylic acid group.

Figure 25:
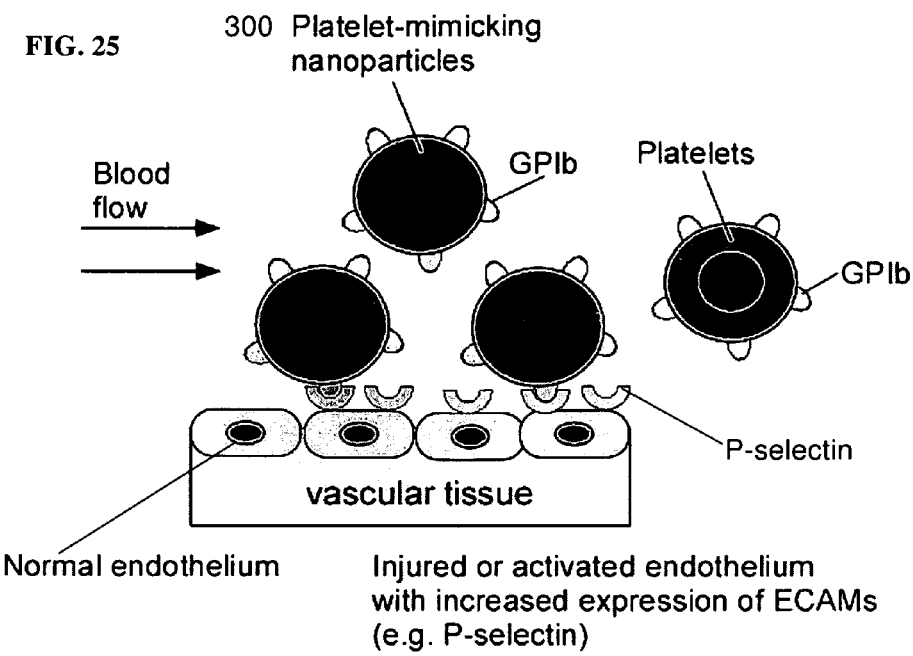
FIG. 25 is a schematic of platelet-mimicking nanoparticles for targeting dysfunctional endothelium.

Temperature sensitive nanoparticles can target and deliver therapeutic agents to treat injured and inflamed ECs after angioplasty and/or stenting treatments. An effective targeting strategy can be determined, where GP Ibα was selected as an ideal ligand for conjugating onto the surface of nanoparticles in order to increase their adhesiveness under high shear conditions. GP Ibα adheres platelets onto the vascular wall in the high shear stress regions and serves as a targeting ligand that binds specifically to P-selectin expressed on activated ECs. As shown in FIG. 25, the platelet-mimicking nanoparticles 200 specifically adhere onto damaged or activated ECs under conditions of high shear stress, inducing cellular retention and uptake of nanoparticles.

Figure 26A:
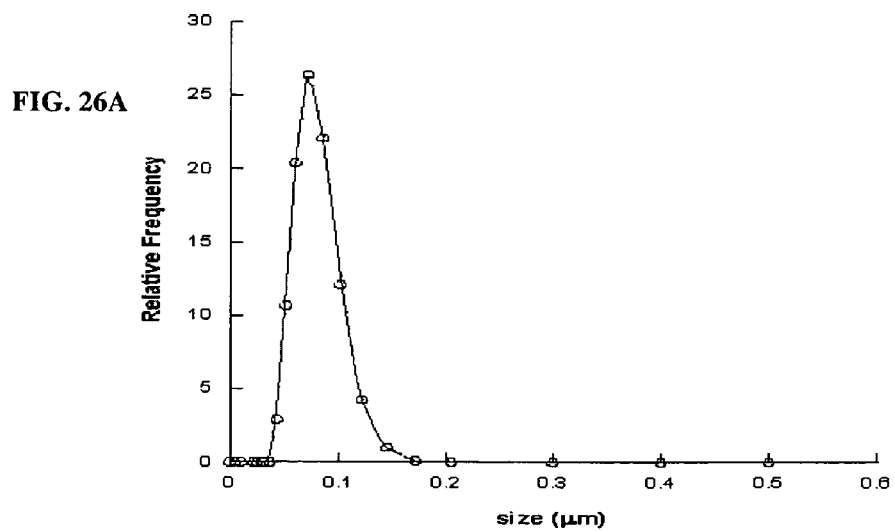
FIG. 26 is a graph of the size distribution of the polystyrene nanoparticles.

Fluoresbrite® YG Carboxylate Polystyrene particles (Polysciences, Inc., Warrington, Pa.) were sputter-coated and observed using an SEM. Nanoparticle size and size distribution were also measured using a laser scattering particle sizer (Nanotrac). The polystyrene nanoparticles used as a model particle were analyzed for size distribution, which showed a mean hydrodynamic diameter of 100 nm with a narrow size distribution, as shown in FIG. 26A. SEM images may also confirm the uniform distribution of polystyrene nanoparticles.

To determine cellular uptake of polystyrene nanoparticles, ECs were seeded onto 24-well plates at a density of 30,000 cells/well and allowed to grow for 2 days. Since high serum media would contribute to the variation in the assessment of particle uptake in ECs, low serum media in all particle uptake studies was used. Low serum growth supplement (LSGS) include 2% fetal bovine serum, hydrocortisone (1 µg/ml), human epidermal growth factor (10 ng/ml), basic fibroblast growth factor (3 ng/ml), and heparin (10 µg/ml). The effects of polystyrene nanoparticle size on cellular particle uptake in ECs was conducted. Polystyrene nanoparticles ranging in size from 100-1000 nm were suspended in low serum growth medium at the concentration of 100 µg/ml. Medium from the 24-well plate was replaced with the particle suspensions, and cells were allowed to incubate with the polystyrene nanoparticles for one hour. The optimize nanoparticle concentration was determined. Nanoparticle solutions (100-800 µg/ml) were prepared in low serum growth medium and added to HAECs for one hour. The effect of incubation time on cellular uptake of polystyrene nanoparticles (~100-nm in size) was evaluated. Cells were incubated with 100 µg/ml nanoparticle solution for various time periods up to 6 hrs. Cells without nanoparticle solutions served as controls.

After experiments, cells were washed carefully at least three times with cold PBS to remove any remaining nanoparticles. After washing, 1 ml of 1% Triton® X-100 was added to each cell sample and incubated for one hour in order to lyse the cells. Twenty-five microliters of cell lysate from each well was used to determine total cell protein content using the BCA protein assay (Pierce) following the manufacturer's instructions. Total protein concentration in each sample was used for normalizing cellular uptake of nanoparticles. To quantify nanoparticle uptake by HAECs, the fluorescent intensity in cell lysates was measured at EM 480 nm/EX 510 nm (VersaFluor™ Bio-Rad Laboratories, Hercules, Calif.). A standard curve was obtained by serial dilution of same stock nanoparticle solutions in 1% Triton® X-100, and the fluorescent intensities were measured using the same filters. The polystyrene nanoparticle uptake by ECs was calculated by normalizing the nanoparticle concentration in each cell lysis sample with the total cellular protein, which correlates to the number of cells in the sample.

Figure 27:
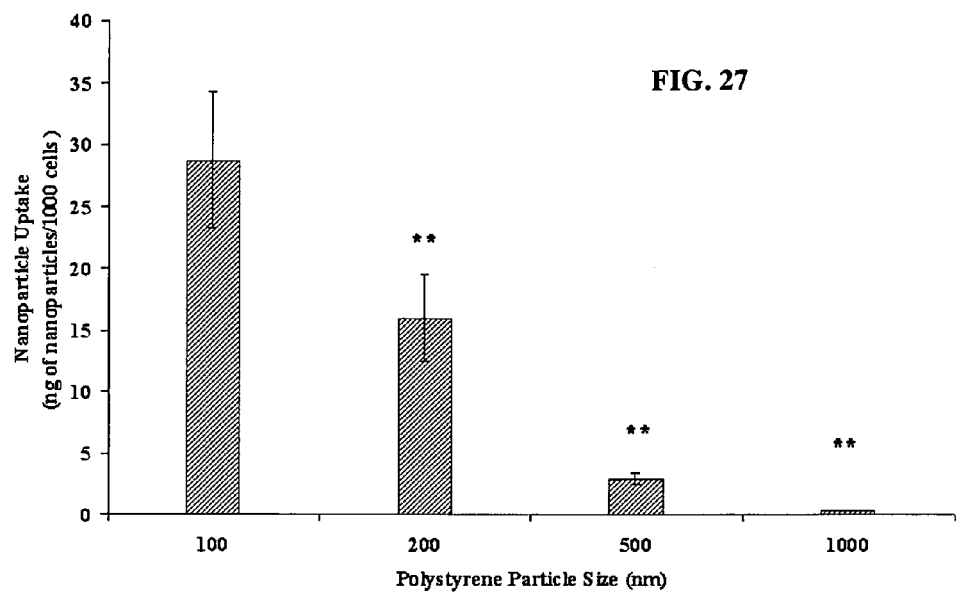
FIG. 27 is a graph of the effects of the particle size on the cellular uptake of polystyrene nanoparticles in ECs, where the values were obtained after one hour of incubation with nanoparticle solutions and represent mean±SD (n=6); & * and ** indicate the significant differences compared to the 100-nm nanoparticle samples (p<0.05 and p<0.001, respectively).

To determine the effects of nanoparticle size on cellular uptake by ECs, experiments were conducted using polystyrene nanoparticles of varying sizes (100-1000 nm) due to their narrow size distribution. A clear trend of decreased cellular uptake when the nanoparticle size was increased. Nanoparticles at the largest size of 1000 nm displayed almost no EC uptake, while the smallest nanoparticle size (100 nm) displayed the highest level of cellular uptake, as shown in FIG. 27.

Figure 28A:
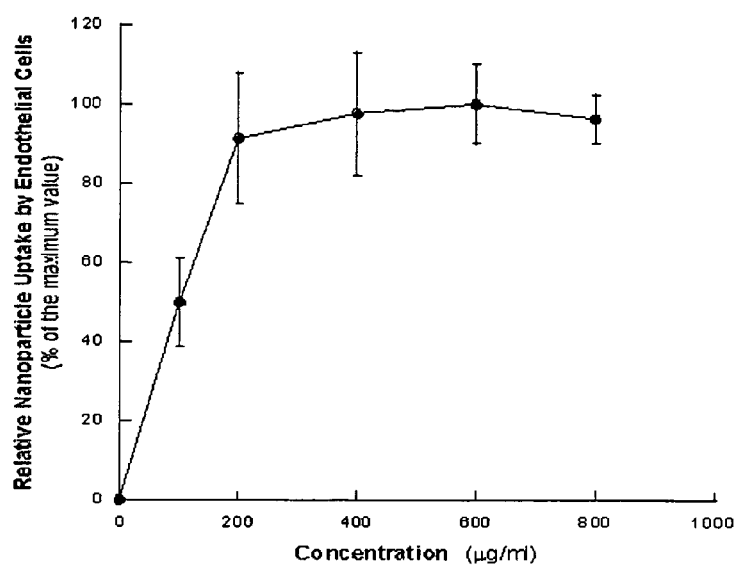
FIG. 28A is a graph of the effects of concentrations on the cellular uptake of 100-nm polystyrene nanoparticles in ECs, where the values were obtained after one hour of incubation with nanoparticle solutions and represent mean±SD (n=6)
Figure 28B:
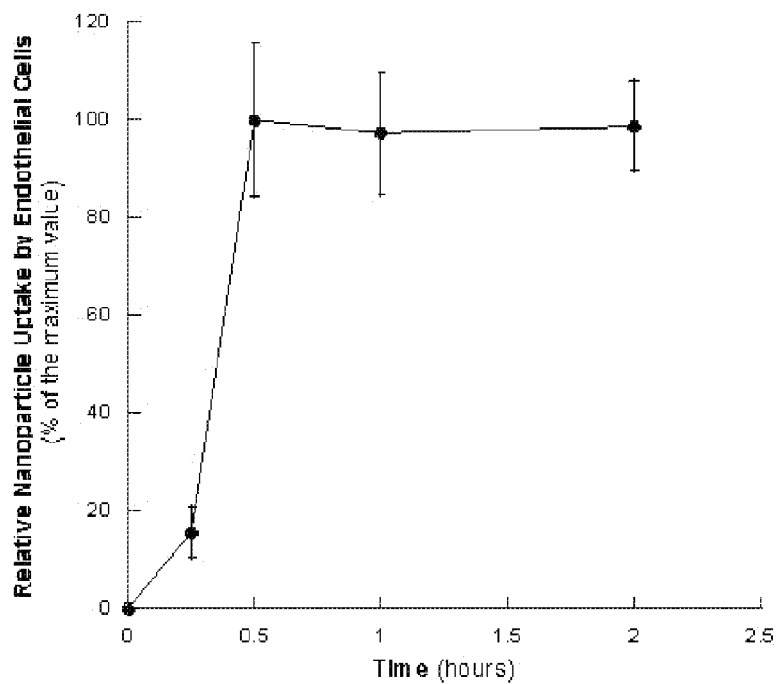
FIG. 28B is a graph of the effects of the incubation time on the cellular uptake of 100-nm polystyrene nanoparticles in ECs, where the samples were incubated with 100 µg/ml of nanoparticle solution and the values represent mean±SD (n=6).

Nanoparticle uptake for 100-nm polystyrene nanoparticles displayed interesting trends for the concentration and incubation time. For the former, cellular uptake by ECs reached saturation at the nanoparticle concentration of 200 µg/ml, as shown in FIG. 28A. For the latter, the saturation was reached in 30 minutes for the polystyrene nanoparticles, as shown in FIG. 28B.

Figure 29:
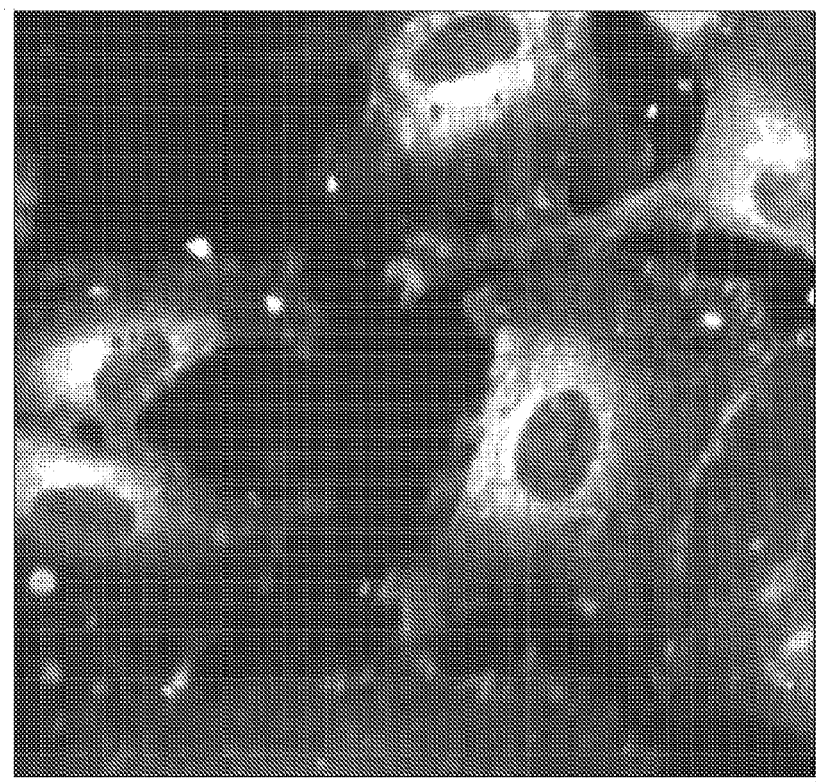
FIG. 29 is a confocal image of the nanoparticle uptake in ECs, where the plasma membranes were dyed using Texas Red® and imaged using a RITC filter, the fluorescent nanoparticles were imaged using a FITC filter, and confocal images represent an overlay of RITC and FITC filters and were taken at Ex($\lambda$) 488 nm, Em($\lambda$) 543 nm.

After experiments, cover slips were washed with cold PBS, followed by the addition of cold FM® 4-64 FX (5 µg/ml of Texas-Red® dye, Invitrogen) in PBS for 10 min to stain cell plasma membranes. ECs were then imaged using a confocal laser scanning microscope (Carl Zeiss LSM Meta 510, Goettingen, Germany) equipped with FITC and RITC filters (Ex (λ) 488 nm, Em(λ) 543 nm). Images of ECs were taken using a fast scan option to section the cells. Slice thickness was set at 1 μm, with an average of 18 slices taken per image. The images were then analyzed using Carl Zeiss LSM Image Browser (version 3.5). Confocal microscopy confirmed the uptake of particles inside the cells, as shown in FIG. 29. Images at the middle point of the cell confirmed that the fluorescent polystyrene nanoparticles were localized inside the cells, whereas those taken at the cell surfaces detected no nanoparticles (data not shown).

Figure 30:
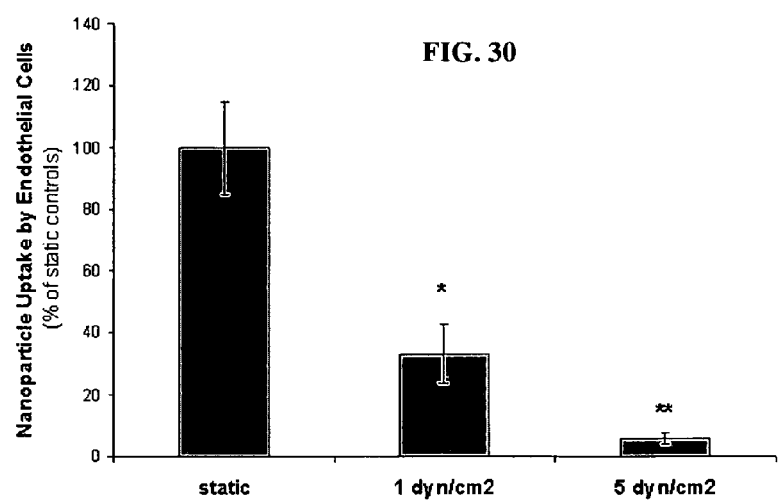
FIG. 30 is a graph of the effects of shear stress on the cellular uptake of 100-nm nanoparticles in HAECs, where values were obtained after one hour of flow with nanoparticle solutions and represent mean±SD (n=8), * and ** indicate the significant differences compared to the 100-nm nanoparticle static samples (p<0.05 and p<0.001, respectively).

The effects of shear stress on cellular uptake of polystyrene nanoparticles by ECs was investigated. Cells were seeded onto pre-etched glass slides at a density of $10^5$ cells/cm$^2$. Upon reaching confluence, cells on glass slides were exposed to either 1 or 5 dyn/cm$^2$ of media containing 100-nm nanoparticles at concentration of 100 μg/ml for 30 minutes using the parallel plate flow chamber system as described previously. The parallel flow chamber was chosen over other flow systems because of its ability to produce constant levels of shear stress. Cells in static conditions served as the control. Analysis of the results was performed using ANOVA and t-tests with $p<0.05$ (StatView 5.0 software, SAS Institute). Post-hoc comparisons were made using the Fisher's least significant differences (LSD). All the results are given as mean±SD. The cellular uptake of nanoparticles was decreased with the increase of shear stress magnitude, as shown in FIG. 30, indicating an inverse correlation between nanoparticle uptake and the levels of shear stress.

Carboxylated nanoparticles, 100 nm in size, were conjugated with glycocalicin using carbodiimide chemistry and avidin-biotin affinity. First, glycocalicin were biotinylated using the Biotin-X—NHS Kit (EMD Biosciences, Inc., San Diego, Calif.) following the manufacturer's instructions. Second, polystyrene nanoparticles were added to a 15 mg/ml EDC solution in 0.1 M MES buffer, pH 4.75 and incubated at room temperature for four hours to ensure carboxyl group activation. After four hours, 500 μg of avidin (EMD Biosciences, Inc.) was added to the nanoparticle solution and allowed to interact overnight in 0.1 M sodium bicarbonate solution (pH 8.5). Biotinylated glycocalicin (120 μl of 50 μg/ml) described in the first step was added to the avidin-conjugated polystyrene nanoparticle solution and reacted at room temperature under gentle agitation, for one hour. The nanoparticle solution was then dialyzed against 0.1 M PBS for three hours to remove any unreacted materials. Great care was taken to avoid exposure of the nanoparticles to light throughout the entire procedure. To confirm the conjugation of ligands onto nanoparticles, 100 μl of 30 μg/ml primary mouse antibody monoclonal against glycocalicin (HIP1, BioLegend), was added to glycocalicin-conjugated nanoparticles in PBS. A fluorescent secondary antibody (anti-mouse IgG1, BioLegend) was added to the nanoparticle solution and incubated for one hour. After washing, nanoparticles were analyzed using flow cytometry/confocal microscopy.

To prepare P-selectin coated surfaces, glass slides were incubated with 500 μl of 20 μg/ml P-selectin (R&D Systems) for four hours at 37° C., followed by one hour of incubation with a 1% BSA solution in PBS to block any nonspecific binding sites. Half the slides were then further incubated with P-selectin antibodies for one hour at room temperature in order to serve as a negative control. The slides were then washed gently with a 0.9% NaCl solution to remove any unbound P-selectin or antibody. To prepare activated ECs, HAECs seeded on glass slides were treated with 25 mM histamine for 12 minutes at room temperature to induce P-selectin expression on ECs. Stimulated (activated) cells were used immediately in flow chamber experiments.

Slides (coated with P-selectin or P-selectin/anti-P-selectin for surface studies and containing an activated EC monolayer for cell studies) were assembled into the parallel plate flow systems that produce 5 dyne/cm$^2$ of shear stress. The nanoparticle solutions were diluted either in PBS for P-selectin/anti-P-selectin surfaces studies or in low serum media for cell studies. After the flow experiments, the amount of nanoparticles bound to the glass cover slides were measured using a fluorometer. The glass slides were also observed using confocal microscopy. The flow chamber experiments totaled 36, where the control nanoparticles, the GP Ibα-conjugated nanoparticles, and the GP Ibα-conjugated+GP Ibα mAbs samples all had 6 P-selectin coated slides and 6 P-selectin/Anti-P-selectin coated slides.

Figure 31:
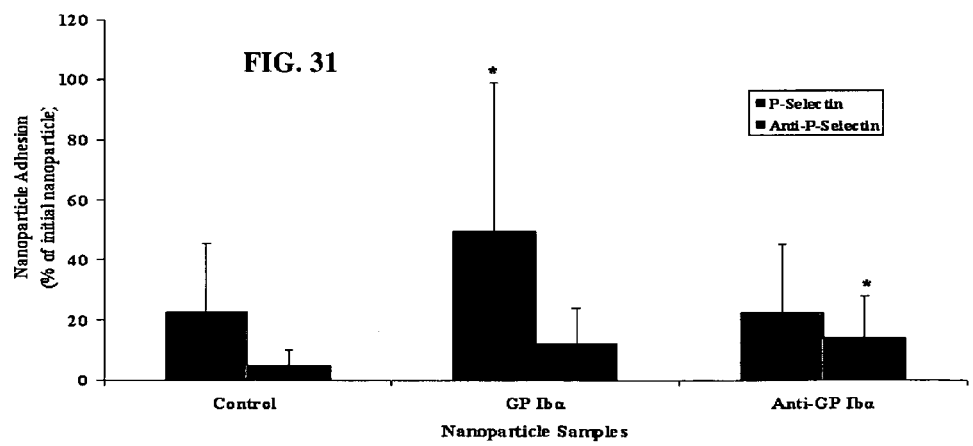
FIG. 31 is a graph of the nanoparticle adhesion onto P-selectin and Anti-P-selectin coated surfaces using different nanoparticle samples, where the values represent mean±SD (n=6), where * indicates the significant differences compared to the control nanoparticle samples (p<0.05).

Specific interaction between P-selectin coated surfaces and GP Ibα-conjugated nanoparticles under flow conditions was analyzed using fluorescent intensity measurements, as shown in FIG. 31. GP Ibα nanoparticles displayed a 60% adhesion rate on P-selectin coated surfaces, while control nanoparticles and nanoparticles samples with pre-incubation of anti-GP Ibα ligands to GP Ibα-conjugated nanoparticles displayed adhesion rates of 19% and 22%, respectively. The control nanoparticles, showed very low adhesion onto both P-selectin and P-selectin/anti-P-selectin surfaces, indicating that non-selective binding under shear stress was minimal. The negative control sample involving anti-GP Ibα-conjugated nanoparticles also showed insignificant levels of adhesion onto P-selectin coated surfaces. In addition, surfaces coated with anti-P-selectin displayed no specific interactions with any of the nanoparticles, with nanoparticle adhesion ranging from 2.5% to 24%. Confocal microscopy analysis of the various slides also confirmed the observation using a fluorometer, with the highest amount of fluorescence detected on P-selectin coated slides subjected to GP Ibα-conjugated nanoparticles (results shown below). These results indicate that GP Ibα-conjugated nanoparticles display an enhanced adhesion onto P-selectin coated surfaces under physiological flow conditions.

Glass slides seeded with activated ECs were run on the flow chamber under the same parameters as the P-selectin/anti-P-selectin coated slides. The results showed significant cellular uptake when GP Ibα nanoparticles were perfused, while other nanoparticles displayed insignificant cellular uptake. Nanoparticles conjugated with GP Ibα displayed much higher uptake in ECs activated with histamine when compared with un-activated EC controls (results not shown). GP Ibα nanoparticles were localized within cellular membranes, with a very low concentration of nanoparticles present in extracellular spaces, as shown in FIGS. 33A-C. Samples were observed at the middle point of each cell using the stack imaging option, with slice thickness set at 1 μm. In contrast, control and GPIb-conjugated nanoparticles were present in extracellular spaces, with minimal nanoparticles observed within the cells, as shown in FIGS. 32A-C and FIGS. 33A-C, respectively. Control nanoparticles had the lowest cellular uptake under exposure to shear stress with almost no nanoparticles seen within the cells, and most nanoparticles were localized on the surface of the glass slides. Conjugation of GPIb onto nanoparticles enhanced cellular uptake in activated endothelial cells as shown in FIGS. 33A-C. These observations confirm that GP Ibα enhanced more cellular uptake of the nanoparticles under conditions of fluid shear stress.

Cellular uptake of polystyrene nanoparticles by ECs decreased as the size of nanoparticles increased, as shown in FIG. 27. Similar to ECs, cellular uptake of polystyrene particles (ranging from 1 to 6 μm) by both leukocytes and macrophages reduced by increasing size of the particles. Alternatively, the maximal cellular uptake of polystyrene particles (ranging from 0.5 to 5 μm in size) was reached when the particle size was 2 μm. For cellular uptake of nanoparticles below 200 nm are internalized in Caco-2 cells and human umbilical vein endothelial cells, where the cells uptake or internalize nanoparticles through receptor-mediated endocytosis process. Understanding the mechanism of cellular nanoparticle uptake plays a large role in intracellular trafficking, thus, greatly modulating the effectiveness of any internalized drug. The results from these studies confirm the advantage of nanoparticles compared to microparticles for intracellular drug delivery; by showing that ECs prefer to uptake only small size particles. Other advantages of nanoparticles include little or no local inflammation and less risk of arterial occlusion.

To enhance recruitment of nanoparticles to endothelial cells under physiological flow conditions, other "endothelial targeting particles" coated with humanized antibodies against E- and P-selectins and "leukocyte-inspired" particles may be used. Micro- and nano-particles may be conjugated with antibodies against P-selectin, the selectin ligand, sialyl Lewis$^x$ (sLe$^x$) and LFA-1 adhere to surfaces coated with P-selectin, E-selectin and ICAM-1 and activated endothelial cells. Similar to leukocyte-inspired nanoparticles, the platelet mimicking nanoparticles mimic the adhesion of platelets on activated endothelial cells were able to adhere to P-selectin coated surfaces under physiological flow conditions. The nanoparticles may also adhere better von Willebrand factor, the ligand of GP Ibα, deposited on injured vessel wall and expressed P-selectin on activated ECs compared to "leukocyte-inspired nanoparticles" due to the higher binding strength of the platelet ligands under high shear stress conditions. Alternative leukocyte-mimicking approaches include endothelial targeting nanoparticles that mimic leukocyte adhesion onto endothelial cells using multiple-receptor targeting: the selectin ligand sLe$^x$ and an antibody against intercellular cell adhesion molecule-1 (ICAM-1). These couple receptors have been involved in the initial dynamic interaction (sLe$^x$) and the firm arrest of leukocytes on the endothelium (ICAM-1). So temperature sensitive nanoparticles with these double ligand bindings of sLe$^x$ and ICAM-1 have a high selective adhesion onto the inflamed endothelium.

vWF's binding action with GP Ibα can occur under much higher fluid shear stress than found in P-selectin mediated adhesion. Finally, the relationship between the bond forces upon the GP Ibα-vWF and/or GP Ibα-P-selectin interaction and shear stress with the size of the particles may be investigated. Alternative studies include conjugated vWF to nanoparticle surfaces and the GP Ibα-conjugated and drug-loaded biodegradable nanoparticles, and development and characterization of drug-loaded endothelial-targeting biodegradable nanoparticles to treat cardiovascular diseases.

Example 2

In Vitro Evaluation of Platelet Mimicking Biodegradable Nanoparticles

Fluorescent dexamethasone (DEX) was formulated and loaded into poly(D, L-lactic-co-glycolic acid) (PLGA) nanoparticles using the standard double emulsion method. Studies of drug release profiles were conducted and cellular uptake studies in HAECs were analyzed using confocal microscopy, fluorescent measurement and protein assays to determine the optimal incubation time and concentration. The effect shear stress on the nanoparticle adhesion and uptake by the HAECs was studied as well as the effect of GpIbα conjugation of PLGA nanoparticles on the nanoparticle adhesion and targeting to P-selectin and vWF coated surfaces under fluid shear stress. Under shear flow conditions, the uptake of nanoparticles decreases significantly and conjugation of PLGA nanoparticles with glycocalicin (the extracellular segment of platelet GP Ibα) significantly increased the particle adhesion on P-selectin and vWF-coated surfaces under physiological flow conditions.

Figure 34:
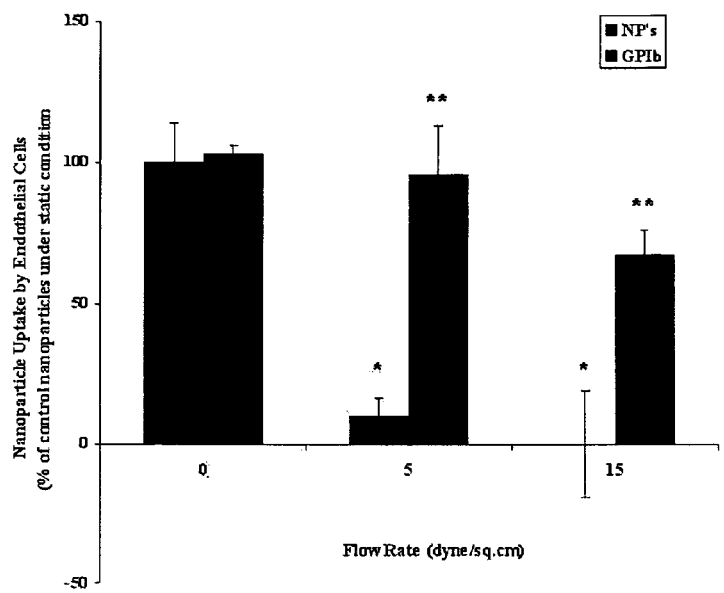
FIG. 34 is a graph of the cellular adhesion of GP Ib conjugated nanoparticles and control nanoparticles by HAECs under varying shear stress, where the values were obtained after 30 minutes of flow with nanoparticle solutions and represent mean±SD (n=3), * indicates the significant differences compared to the control nanoparticle static samples (p<0.001), and ** indicates the significant differences compared to the control nanoparticles (p<0.001) at each flow rate.

GP Ibα was selected as an ideal ligand for conjugating onto the surface of nanoparticles in order to increase their adhesiveness under high shear conditions. GP Ibα adheres platelets onto the vascular wall in the high shear stress regions and serves as a targeting ligand that binds specifically to P-selectin expressed on activated ECs. As shown in FIG. 34, the platelet-mimicking nanoparticles specifically adhere to the damaged or activated ECs under high shear stress conditions encouraging increased cellular retention and uptake of nanoparticles.

Figure 35C:
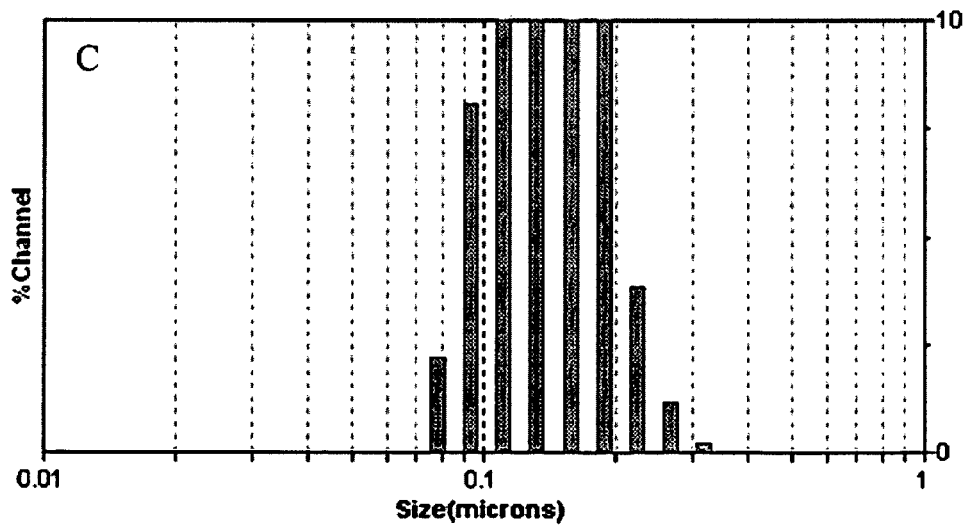
FIG. 35C is a graph of the size distribution of the PLGA nanoparticles.

The PLGA nanoparticles were formulated using the standard double emulsion techniques and freeze-dried for 72 hours. A nanoparticle solution of 5 mg/ml was prepared in DI water and a drop was placed on a coverslip. The coverslip was sputter-coated and observed using an SEM for size characterization. The sample was also imaged using TEM for size, as shown in FIGS. 35A-B. Nanoparticle size and size distribution were also measured using a laser scattering particle sizer (Nanotrac), as shown in FIG. 35C. From these images it can be concluded that the average size of the PLGA nanoparticles is 160 nm.

To determine cellular uptake of PLGA nanoparticles, ECs were seeded onto 24-well plates at a density of 30,000 cells/well and allowed to grow for 2 days. 12 hours before the experiment, the cells were incubated with serum free media. To determine the optimal uptake concentration of the PLGA nanoparticles, nanoparticle solutions (0-300 μg/ml) were prepared in serum free medium and incubated with HAECs for one hour. The optimal incubation time for the nanoparticle uptake, ECs were incubated with 100 μg/ml nanoparticle solution for various time periods up to 6 hrs was evaluated. Cells without nanoparticle solutions served as controls.

After experiments, cells were washed carefully at least three times with cold PBS to remove any remaining nanoparticles. After washing, 1 ml of 1% Triton® X-100 was added to each cell sample and the cells were incubated for one hour in order to lyse them. Twenty-five microliters of cell lysate from each well was used to determine total cell protein content using the BCA protein assay (Pierce) following the manufacturer's instructions. Total protein concentration in each sample was used for normalizing cellular uptake of nanoparticles. To quantify nanoparticle uptake by HAECs, the fluorescent intensity in cell lysates was measured at EM 480 nm/EX 510 nm (VersaFluor™, Bio-Rad Laboratories, Hercules, Calif.). A standard curve was obtained by serial dilution of same stock nanoparticle solutions in 1% Triton® X-100, and the fluorescent intensities were measured using the same filters. The PLGA nanoparticle uptake by ECs was calculated by normalizing the nanoparticle concentration in each cell lysis sample with the total cellular protein, which correlates to the number of cells in the sample. Nanoparticle uptake of PLGA nanoparticles by ECs reached saturation at the nanoparticle concentration of 200 μg/ml, as shown in FIG. 36A and the optimal incubation time was found to be four hours, as shown in FIG. 36B.

For confocal imaging, cells were seeded on coverslips and allowed to grow to confluence. After uptake experiments, cover slips were washed with cold PBS, followed by the addition of cold FM® 4-64 FX (5 µg/ml of Texas-Red® dye, Invitrogen) in PBS for 10 min to stain cell plasma membranes. ECs were then imaged using a confocal laser scanning microscope (Leica) equipped with FITC and RITC filters (Ex($\lambda$) 488 nm, Em($\lambda$) 543 nm). Images of ECs were taken using a fast scan option to section the cells. Slice thickness was set at 1 µm, with an average of 18 slices taken per image. The images were then analyzed using Carl Zeiss LSM Image Browser (version 3.5). Confocal microscopy confirmed the uptake of particles inside the cells, as shown in FIGS. 37A-B. Images at the middle point of the cell confirmed that the fluorescent PLGA nanoparticles were localized inside the cells. Those taken at the cell surfaces detected no NPs.

To determine the cytotoxic effects of the PLGA nanoparticles on the ECs, LDH assay was performed on the ECs using the manufacturer's instructions. From FIG. 38 it can be seen that even at high concentrations of 1000 µg/ml the nanoparticles exhibit minimal cytotoxicity compared to the positive triton control.

Figure 39:
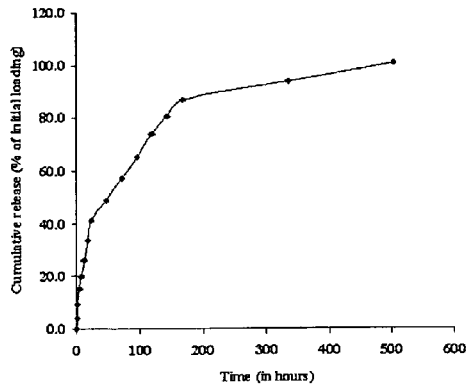
FIG. 39 is a graph of in vitro release profile of dexamethasone (DEX) from PLGA nanoparticles at 37° C. over 3 weeks (504 hours).

The drug (DEX) loaded PLGA nanoparticles were observed for the drug release behavior. About 200 µg/ml of nanoparticle solution (n=4) was prepared in PBS and the nanoparticle solution was placed inside dialysis bags with a MWCO of 100,000 kDa. Samples were then dialyzed against PBS at 37° C. At pre-determined time points, 1 ml of the dialysate was removed from each sample and stored at −20° C. for later analysis. Dialysate volume was reconstituted by adding 1 ml of fresh PBS to each sample. Dialysate samples were analyzed using the microplate reader at a wavelength of 242 nm. The loading efficiency of DEX was determined according to Equation (3) and was found to be about 60%. Percent cumulative release of DEX exhibited a sustained release for over 2 weeks, as shown in FIG. 39.

$$\% \text{ Loading Efficiency} = \frac{\text{total drug used in formulation} - \text{drug present in solution}}{\text{total drug used}} \times 100\% \quad (3)$$

Figure 40:
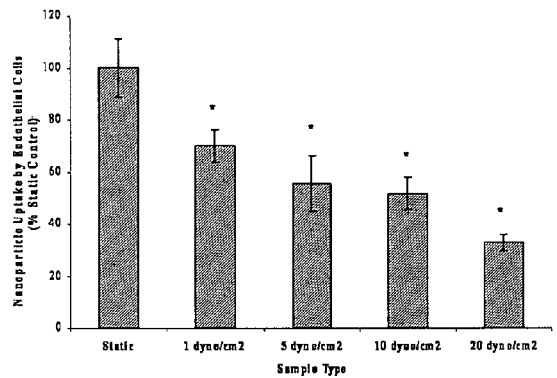
FIG. 40 represents the effects of shear stress on the cellular uptake of PLGA nanoparticles in HAECs, where values were obtained after 30 minutes of flow with the PLGA nanoparticle solutions and represent mean±SD (n=4), and * indicate the significant differences compared to the static nanoparticle samples (p<0.05 respectively).

The effects of shear stress on cellular uptake of PLGA nanoparticles by ECs was investigated. Cells were seeded onto pre-etched glass slides at a density of $10^5$ cells/cm$^2$. Upon reaching confluence, cells on glass slides were exposed to varying flow rates (0 to 20 dyn/cm$^2$) of media containing PLGA nanoparticles at concentration of 200 µg/ml for 30 minutes using the parallel plate flow chamber system as described previously. The parallel flow chamber was chosen over other flow systems because of its ability to produce constant levels of shear stress. Cells in static conditions served as the control. Analysis of the results was performed using ANOVA and t-tests with $p<0.05$ (StatView 5.0 software, SAS Institute). Post-hoc comparisons were made using the Fisher's least significant differences (LSD). All the results are given as mean±SD. The cellular uptake of nanoparticles decreased with the increase of shear stress magnitude, as shown in FIG. 40. This shows that an inverse relation exists between nanoparticle uptake and the shear stress level.

PLGA nanoparticles were conjugated with glycocalicin using carbodiimide chemistry and avidin-biotin affinity. First, glycocalicin were biotinylated using the Biotin-X-NHS Kit (EMD Biosciences, Inc.) following the manufacturer's instructions. Second, PLGA nanoparticles were added to a 15 mg/ml EDC solution in 0.1 M MES buffer, pH 4.75 and incubated at room temperature for four hours to ensure carboxyl group activation. After four hours, 500 µg of avidin was added to the nanoparticle solution and allowed to interact overnight in 0.1 M sodium bicarbonate solution (pH 8.5). Biotinylated glycocalicin (120 µl of 50 µg/ml) was added to the avidin-conjugated PLGA nanoparticle solution and reacted at room temperature under gentle agitation, for one hour. The nanoparticle solution was then dialyzed against 0.1 M PBS for three hours to remove any unreacted materials. Great care was taken to avoid exposure of the nanoparticles to light throughout the entire procedure. To confirm the conjugation of ligands onto nanoparticles, 100 µl of 30 µg/ml primary mouse antibody monoclonal against glycocalicin (HIP1, BioLegend), was added to glycocalicin-conjugated nanoparticles in PBS. A fluorescent secondary antibody (antimouse IgG1, BioLegend) was added to the nanoparticle solution and incubated for one hour. After washing, nanoparticles were analyzed using confocal microscopy.

To prepare P-selectin and vWF coated surfaces, glass slides were incubated with 500 µl of 20 µg/mlP-selectin and vWF (R&D Systems) for four hours at 37° C., followed by one hour of incubation with a 1% BSA solution in PBS to block any nonspecific binding sites. Half the slides were then further incubated with P-selectin and vWF antibodies for one hour at room temperature in order to serve as a negative control. The slides were then washed gently with a 0.9% NaCl solution to remove any unbound protein or antibody. To prepare activated ECs, HAECs seeded on glass slides as described earlier were treated with 25 mM histamine for 12 minutes at room temperature to induce P-selectin expression on ECs. Stimulated (activated) cells were used immediately in flow chamber experiments.

Slides (coated with P-selectin, vWF or P-selectin/anti-P-selectin and vWF/anti-vWF) for surface studies were assembled into the parallel plate flow systems that produce 5 dyne/cm$^2$ of shear stress. The nanoparticle solutions were diluted in PBS for surfaces studies. After the flow experiments, the amount of nanoparticles bound to the glass cover slides were measured using a fluorometer. The glass slides were also observed using confocal microscopy.

Figure 41:
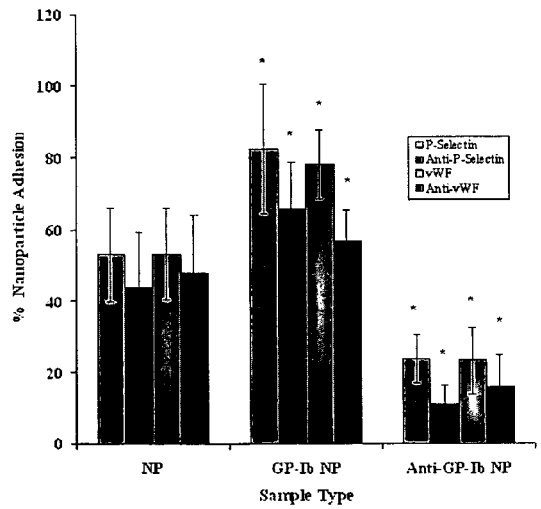
FIG. 41 is a graph of the PLGA nanoparticle adhesion onto P-selectin, vWF, Anti-P-selectin and Anti-vWF coated surfaces using control and conjugated nanoparticle samples, where the values represent mean±SD (n=4), and * indicates the significant differences compared to the control nanoparticle samples (p<0.05).

Specific interaction between P-selectin and vWF coated surfaces and GP Ibα-conjugated nanoparticles under flow conditions was analyzed using fluorescent intensity measurements, as shown in FIG. 41. GP Ibα nanoparticles displayed an 85% adhesion rate on P-selectin coated surfaces and 80% adhesion rate on vWF coated surfaces, while control nanoparticles and nanoparticles samples with pre-incubation of anti-GP Ibα ligands to GP Ibα-conjugated nanoparticles displayed adhesion rates of 55%. The control nanoparticles, showed very low adhesion onto P-selectin, vWF, P-selectin/anti-P-selectin and vWF/anti-vWF surfaces, indicating that non-selective binding under shear stress was minimal. The negative control sample involving anti-GP Ibα-conjugated nanoparticles also showed insignificant levels of adhesion onto P-selectin and vWF coated surfaces. In addition, surfaces coated with anti-P-selectin and anti-vWF displayed no specific interactions with any of the nanoparticles, with nanoparticle adhesion of 5% and 20%.

Example 3

Prostate Specificity of Cell Permeable Peptides (CPPs) R11

To screen CPPs for optimal intracellular delivery of drugs in prostate cancer cells, FITC-tagged peptides: TAT (G-RKKRRQRRR, SEQ ID NO: 1), PENE (G-RQIKIW- FQNRRMKWKK, SEQ ID NO: 2), KALA (G-KLALKLA-LKALKAALKLA, SEQ ID NO: 3), homopolymers of L-arginine R11 (G-$R_{11}$), and homopolymers of L-lysine K11 (G-K11) at different concentrations (0, 0.1, 1, 5 μM) were incubated with four prostate cancer cell (PCa) lines (LNCaP, PC3, C4-2, and LAPC4 cells) for 30 minutes, as shown in Zhou, J et al. "Inhibition of Mitogen-Elicited Signal Transduction and Growth in Prostate Cancer with a Small Peptide Derived from the Functional Domain of DOC-2/DAB2 Delivered by a Unique Vehicle", Cancer Res 2006; 66: (18) Sep. 15, 2006, incorporated by reference herein. A dose-dependent CPP uptake by four different PCa cells was observed (the fluorescent intensity of cell lysis samples was determined by a fluorometer with excitation 490-500 nm, emission 515-525 nm). Of those five studied CPPs, R11 exhibited the highest uptake in all four PCa cell lines (at least a 6-fold increase). The half-life of R11 in each cell line was studied by incubating cells with FITC-labeled R11 (5 μM) for 30 minutes. The half-life of R11 was 23.4, 24.1, 22.8, and 24.0 hours in LNCaP, C4-2, LAPC4, and PC3, respectively. R11 has its in vitro half-life at about 23-24 hours, indicating its high stability for use.

Although R11 peptide is highly internalized by various prostate cancer cells, it may not consist of prostate specificity. Thus, R11's specificity in prostate tissues in vivo was studied by using nude mouse models. Interestingly, the R11 peptide exhibited preferential uptake in prostate and bladder tissues during the in vivo evaluation of tissue distribution of FITC-tagged R11 in nude mice. The R11 peptide was accumulated the highest in prostate and bladder tissues and the lowest in other organs such as liver, lungs, muscle, and kidneys. And the R11 was conjugated with a bifunctional chelator, DOTA (1,4,7,10-Tetraazacyclo-dodecane-1,4,7,10-tetraacetic acid) so that R11 could be radiolabeled with $^{64}Cu$. Results from the injection of purified $^{64}Cu$-DOTA-R11 with a range of 5-10 μCi in nude mice also showed that $^{64}Cu$-DOTA-R11 was accumulated strongest in prostate and bladder tissues. Again, this peptide exhibited remarkably low uptake in other organs such as blood, lungs, livers, spleen, kidneys, and muscle.

Figure 42:
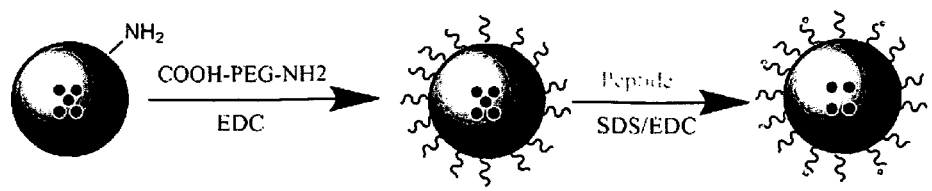
FIG. 42 is a schematic of conjugating peptides to the functionalized copolymer magnetic nanoparticles.

In summary, the results demonstrated the formulation of the core-shell polymer magnetic nanoparticles with a responsive temperature above body temperature and functional amine groups for conjugation of specific molecules absorbed by only prostate cancer cells. R11 peptides were highly internalized by prostate cancer cells and specifically absorbed by prostate tissues was found, which support that the functionalized copolymer magnetic nanoparticles tagged with R11 peptides presents an ideal model carrier for drug delivery to prostate tumors and/or prostate cancer cells. R11 peptides may be attached to functionalized copolymer magnetic nanoparticles through PEG bifunctional groups that are conjugated to allylamine, as shown in FIG. 42.

Example 4

Therapeutic Effectiveness Using an Orthotopic Mouse Model

In order to appropriately establish copolymer magnetic nanoparticle drug delivery construct as an effective treatment for prostate cancer, in vivo studies are needed. To test copolymer magnetic nanoparticle for effective prostate cancer treatment, an orthotropic mouse model of prostate cancer may be developed for the in vivo observation of copolymer magnetic nanoparticle drug carriers within the tumor regions. After treatment, these animals are monitored for tumor growth using physical examination, weights, and calipers to measure tumor size changed over time. At a predetermined time, the animals are processed further with MRI imaging. The animals are then sacrificed, and the organs such as the thyroid, livers, kidneys, bladder, prostate, and lungs are processed for iron content and tissue integrity using standard histological methods.

To generate prostate tumors on nude mice, male NCr-nu/nu (Nude) mice receive an injection of $2 \times 10^5$ cells/mL of prostate cancer cells PC3. NCr-nu/nu are immunodeficient, lacks a thymus, is unable to produce T-cells. This technique has been established to produce prostate tumors in mice. In brief, the mice are anesthetized, and the cancer cell suspension is injected into the identified prostate gland. These animals are monitored for tumor growth using physical examination, weights, and calipers to measure tumor size. After several weeks, the mice bearing a tumor volume of 100 to 200 mm³ are selected for treatments with the drug-loaded functionalized copolymer magnetic nanoparticles.

To perform the in vivo studies in order to determine the effectiveness of the functionalized copolymer magnetic nanoparticles, mice with a tumor developed to an approximate size are injected with various doses of the functionalized copolymer magnetic nanoparticles to find the optimal dose. A range of doses (0, 20, 40, and 60 mmole Fe/kg) are used. The functionalized copolymer magnetic nanoparticles dose that gives the most reduction in tumor growth and the least side effects would be chosen as the optimal dose for further studies. Animals are randomly divided into different groups as shown in Table 4. Treatment T1 animals are exposed to the drug loaded functionalized copolymer magnetic nanoparticles. Treatment group T2 animals are for magnetic targeting, the functionalized copolymer magnetic nanoparticles are injected and magnets are applied to the prostate glands for 30 minutes. For the T3 group of animals, thermotherapy is performed immediately after magnetic targeting of T2. For the thermotherapy, the functionalized copolymer magnetic nanoparticles are injected when a magnetic belt is applied for 30 minutes at the tumor region, then the nanoparticles are subsequently heated in an externally applied AC magnetic field. The used AC magnetic field applicator system (MFH 12-TS, MagForce Nanotechnologies GmbH) operates at the frequency of 100 kHz and a certain range of field strength (0-18 kA/m). The AC magnetic field strength is gradually increased to produce the actual heat from the magnetic nanoparticles (around 12.6 kA/m). Using tolerable H-field-strengths of 3.0-6.0 kA/m in the pelvis, up to 7.5 kA/m in the thoracic and neck region and >10.0 kA/m for the head, specific absorption rates of 60-380 W/kg in the target leading to a 40° C. heat-coverage of 86% was achieved.

TABLE 4

Overview of animal study groups (12 animals per group)

| Group | Treatment |
|---|---|
| C1 | Tumor growth controls, no treatment |
| C2 | Sham (saline injection, 100 μl saline) plus magnetic field exposure |
| C3 | 100 μl of saline with bare magnetic nanoparticles at an optimal dose |
| C4 | 100 μl of saline containing drugs (doxorubicin) |
| T1 | 100 μl of saline containing optimal dose of drug loaded PMNP |
| T2 | 100 μl of saline containing drug loaded PMNP, magnets at the prostate for magnetic targeting |
| T3 | 100 μl of saline containing drug loaded PMNP, magnets at the prostate, thermotherapy 30 min |

To assess the effectiveness of the functionalized copolymer magnetic nanoparticles, mouse blood is collected by tail-tip resection into anticoagulant (ACD) tubes at different time points (1, 3, and 7 days) after treatments for further analysis. At the end point, the animals are processed further with MRI using the 4.7T Varian small animal scanner with the following imaging parameters: the T2-weighted spin-echo sequence: 4000/30 (TR msec/TE msec), field of view 60 mm×30 mm, matrix of 128×128, and section thickness of 2 mm and the T2*-weighted gradient-echo sequence: 500/40 (ms), field of view 60×30 mm, flip angle of 20°, matrix of 128×128, and section thickness of 2 mm. Animals are then sacrificed for histological and morphological analysis of tissue sections using standard histological methods. Tumors in each mice group are dissected, and tumor size is weighed and measured. Furthermore, the thyroid, livers, kidneys, spleen, bladder, prostate and lungs are dissected and assayed to determine drug and nanoparticle (Fe content) accumulation. In addition, some sections are stained with hematoxylin & eosin to detect cells and tissue integrity, whereas other sections are stained with Perls Prussian blue to identify Fe regions (localization of magnetic nanoparticles). The sections are photographed under the image analysis system (Nikon Camera), and a morphometric analysis is performed by an observer blinded to the treatment regimen.

Example 5

Medical Applications

The magnetic core of functionalized copolymer magnetic nanoparticles may be used for guiding the system using external magnetic field and providing image capability through Magnetic Resonance Imaging (MRI). MRI, or nuclear magnetic resonance imaging (NMRI), is used in radiology to visualize the structure and function of the body to provide detailed images of the body in any plane. MRI provides great contrast between the different soft tissues of the body, making it especially useful in neurological (brain), musculoskeletal, cardiovascular, and oncological (cancer) imaging. MRI uses a powerful magnetic field to align the nuclear magnetization of (usually) hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to construct an image of the body and the functionalized copolymer magnetic nanoparticles.

Figure 43:
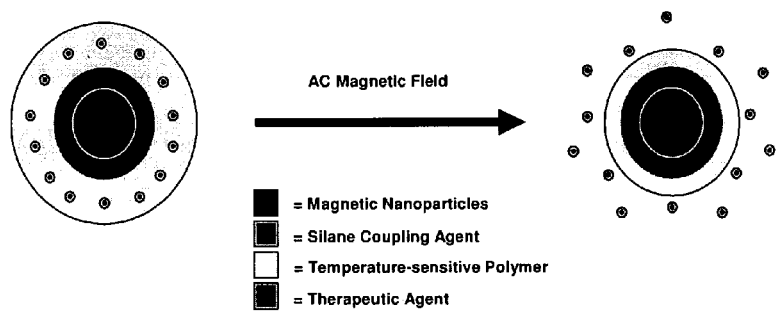
FIG. 43 is a schematic of one principle of the controlled drug release via a magnetic field.

Also, the functionalized copolymer magnetic nanoparticles may be coupled with the use of magnetic guidance to efficiently target tumor cells. The functionalized copolymer magnetic nanoparticles may provide modality imaging probes (magnetic nanoparticles as a core of multi-layer copolymer nanoparticles) for optimizing and assessing the efficiency of this system as a drug carrier. Alternatively, the magnetic core of the functionalized copolymer magnetic nanoparticles may induce temperature for hyperthermia therapy. Alternatively, the functionalized copolymer magnetic nanoparticles may be used a method of heat-generation, which causes drug release from the temperature-sensitive polymeric shell, as shown in FIG. 43. The application of an external magnetic field results in the accumulation of magnetic nanoparticles at a target site. The use of heat to provide a temperature controlled drug release due to the temperature-sensitive property of the shell polymer. Alternatively, the functionalized copolymer magnetic nanoparticles can be loaded to a stent at any time with any dosage due to its magnetic properties to prevent restenosis.

Figure 44:
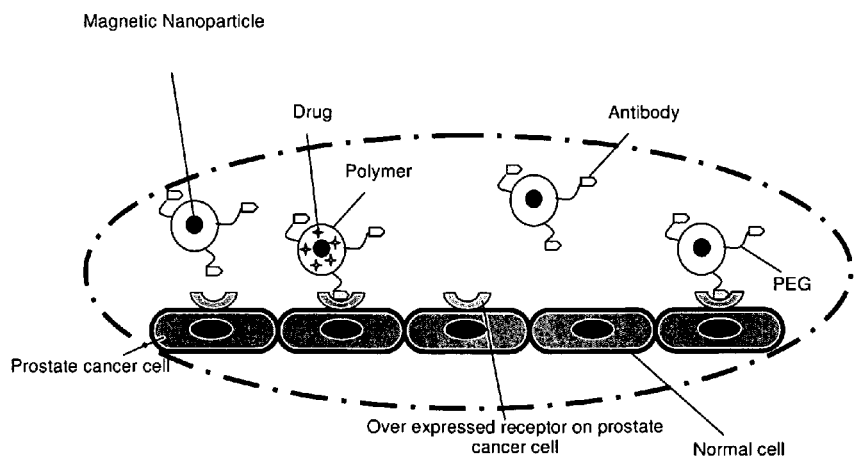
FIG. 44 is a schematic of one scheme for the functionalized copolymer magnetic nanoparticles.

The temperature sensitive nanoparticles are specific and eliminate the unwanted side effects, e.g. weakness, damage to different organs, and hair lost (that conventional systematic drug delivery system has). Furthermore, the functionalized copolymer magnetic nanoparticles give the ability to monitor their quantity and location at targeted site. The functionalized copolymer magnetic nanoparticles are sensitive due to the high dense magnetic nanoparticles that can be visualized. Furthermore, this system is very specific that even one cell can be tagged inside body where the image can be seen. The specificity of this system is due to the novel copolymer that enables the conjugation of antibody to the system. The functional groups can be configured with various molecules possessing compatible binding ligands and/or antibodies to detect to a particular molecule or cell of interest or bound to biodegradable cross-linking agents, as shown in FIG. 44.

To investigate the imaging properties of the synthesized nanoparticles, the contrast properties of original magnetic nanoparticles and the copolymer PMNP may be investigated using MRI imaging. Aqueous particle suspension with different concentrations ([Fe]=0.001-1 mM) in tubes placed in the 2 cm volume coil (slice thickness=2 mm, field of view FOV=3 cm×3 cm, using a 128×128 imaging matrix and an average of two acquisitions). All imaging experiments are performed on a 4.7T Varian small animal MRI scanner. The imaging protocol consists of spin-echo sequences with two sets of timing parameters: a fixed echo time TE of 12 ms and varying repetition time, and TR with 12 data points from 200 ms to 6 s for the T1 determination, and a fixed TR of 4 s and varying TE with 8 data points from 12 ms to 120 ms for the T2 determination. In addition, nanoparticles would be localized in agarose gel by placing them between two permanent magnets creating a uniform magnetic field. MRI imaging is used to measure the location and quantity of the magnetic nanoparticles. The concentration of nanoparticles is correlated with the intensity of nanoparticles in the image produced in the MRI. Movement of these nanoparticles in agarose gels using different magnetic fields may also be investigated.

Alternatively, to overcome the weak magnetic responsiveness (i.e. requiring a much higher external magnetic field), implanting magnets to the target site is used to maximize the magnetic field at that location. For instance, the functionalized copolymer magnetic nanoparticles loaded with the chemotherapy agent doxorubin have accumulated better at a kidney implanted with an Au-plated magnet as shown in previous studies in rabbit studies. Another strategy is using other targeted motifs in order to enhance the targeting ability of the copolymer MNP's as proposed in project for specific peptides R11. Alternatively, incorporating other molecules such as antibodies or specific adaptamers specifically bound to prostate cancer cells can also be applied.

What is claimed is:

1. A copolymeric magnetic nanoparticle comprising a magnetic core, a copolymeric shell comprising temperature sensitive properties, and an outer surface, wherein the copolymeric shell comprises
   1) a copolymer comprising the monomers
      i) N-isopropylacrylamide;
      ii) acrylamide; and
      iii) allylamine or a derivative or analog thereof; and
   2) a therapeutic agent,
wherein the outer surface comprises a plurality of functional groups from the monomer of part iii) for conjugation to a substance selected from the group consisting of a biomolecule, a bioactive molecule, an antibody and a specific ligand, wherein the copolymeric magnetic nanoparticle allows controlled release of the therapeutic agent in response to a change in temperature, wherein the magnetic core further comprises a plurality of magnetic nanoparticles covalently bound with a vinyl trimethoxysilane.

2. The copolymeric magnetic nanoparticle of claim 1, wherein the copolymeric shell is characterized by a lower critical solution temperature that is above body temperature.

3. A method of drug delivery comprising loading the copolymeric magnetic nanoparticle of claim 1 with at least one therapeutic agent, guiding the copolymeric magnetic nanoparticle with an external magnetic field, and allowing controlled drug release in response to a change in temperature.

4. The method of drug delivery in claim 3, wherein the magnetic core further comprises a plurality of magnetic nanoparticles covalently bound with vinyl trimethoxysilane.

5. The method of drug delivery in claim 3, wherein the copolymer is functionalized with an amine group wherein biomolecules can attach.

6. The method of drug delivery in claim 3, wherein the biomolecule binds to an activated endothelial cell.

7. A composition for drug delivery comprising: a plurality of nanoparticles of claim 1 conjugated with glycocalicin to increase the nanoparticle adhesion to activated endothelial cells and cellular uptake of nanoparticles under physiological flow conditions.

8. The composition of claim 7, wherein glycocalicin is conjugated to nanoparticles through an avidin-biotin complex.

9. The composition of claim 7, wherein the nanoparticles include a size of substantially 100 nm.

10. The composition of claim 7, wherein the nanoparticles are conjugated to sialyl Lewis$^x$ and intercellular cell adhesion molecule-1.

* * * * *